(12) United States Patent
Oldfield et al.

(10) Patent No.: US 8,609,638 B2
(45) Date of Patent: Dec. 17, 2013

(54) ENZYME INHIBITING COMPOUNDS AND METHODS

(75) Inventors: Eric Oldfield, Champaign, IL (US); Ke Wang, Urbana, IL (US); Weixue Wang, Urbana (IL); Yonghui Zhang, Urbana (IL)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/500,845

(22) PCT Filed: Oct. 8, 2010

(86) PCT No.: PCT/US2010/052049
§ 371 (c)(1),
(2), (4) Date: Apr. 6, 2012

(87) PCT Pub. No.: WO2011/044505
PCT Pub. Date: Apr. 14, 2011

(65) Prior Publication Data
US 2012/0196835 A1    Aug. 2, 2012

Related U.S. Application Data

(60) Provisional application No. 61/249,929, filed on Oct. 8, 2009.

(51) Int. Cl.
*A61K 31/675* (2006.01)
*A61K 31/6615* (2006.01)
*C07F 9/40* (2006.01)
*C12N 9/99* (2006.01)

(52) U.S. Cl.
USPC ............ 514/89; 435/4; 435/184; 514/82; 514/106; 514/108; 514/574; 546/22; 558/152; 558/155

(58) Field of Classification Search
USPC ............ 514/89, 82; 435/4, 183; 546/22
See application file for complete search history.

(56) References Cited

U.S. PATENT DOCUMENTS

| 4,588,828 | A | 5/1986 | Bisacchi et al. |
|---|---|---|---|
| 4,654,426 | A | 3/1987 | Bisacchi et al. |
| 7,286,973 | B1 | 10/2007 | Noel et al. |
| 7,402,408 | B2 | 7/2008 | Bacher et al. |
| 2006/0249067 | A1 | 11/2006 | Rayner et al. |
| 2008/0206267 | A1 | 8/2008 | Jomaa et al. |
| 2009/0176781 | A1 | 7/2009 | Want et al. |

OTHER PUBLICATIONS

Y. Tanaka et al. Medicinal Chemistry, 2007, 3, 85-99.*

(Continued)

*Primary Examiner* — Savitha Rao
*Assistant Examiner* — Angela Brown-Pettigrew
(74) *Attorney, Agent, or Firm* — Haukaas Fish PLLC; Michael H. Haukaas

(57) ABSTRACT

The invention provides compounds, compositions, and methods for studying the Rohmer pathway and for treating bacterial infections or parasitic infections. The parasitic infection can be a protozoan infection, such as malaria. The compounds and compositions can also be used as antibiotics, for example, to kill bacteria or parasites, or to inhibit bacterial or parasite growth. The invention further provides inhibitors of isoprenoid biosynthesis enzymes, and methods of inhibiting the activity of isoprenoid biosynthesis enzymes. The compounds can be, for example, alkynes or allenes that bind to a unique Fe of an Fe4S4 cluster of an isoprenoid biosynthesis enzyme.

26 Claims, 5 Drawing Sheets

Acetylene Series:

(56) References Cited

OTHER PUBLICATIONS

Nagaki, M. et al. Substrate specificities of farnesyl diphosphate synthases of *Bacillus stearothermophilus* and porcine liver with allylic substrate homologs having vinyl or ethynyl group. Journal of Molecular Catalysis B: Enzymatic. 2009, 59, pp. 163-167.

Hosokawa, A. et al. Evaluation of an Alkyne-containing Analogue of Farnesyl Diphosphate as a Dual Substrate for Protein-prenyltransferases. International Journal of Peptide Research and Therapeutics. 2007, 13(1-2), pp. 345-354.

Leon, A. et al. Isoprenoid Biosynthesis as a Drug Target: Bisphosphonate Inhibition of *Escherichia coli* K12 Growth and Synergistic Effects of Fosmidomycin. J. Med. Chem. 2006, 49, pp. 7331-7341.

Szabo, C. et al. An Investigation of Bone Resorption and *Dictyostelium discoideum* Growth Inhibition by Bisphosphonate Drugs. J. Med. Chem. 2002, 45, pp. 2894-2903.

Wu, Z., Wouters, J., et al. Isopentenyl Diphosphate Isomerase. Mechanism-Based Inhibition by Diene Analogues of Isopentenyl Diphosphate and Dimethylallyl Diphosphate. J. Am. Chem. Soc. 2005, 127, pp. 17433-17438.

Eberl, M., et al. Microbial isoprenoid biosynthesis and human [gamma][delta] T cell activation. FEBS Letters, 2003, 544, pp. 4-10.

Ghosh, S. et al. Effects of Bisphosphonates on the Growth of *Entamoeba histolytica* and *Plasmodium* Species in Vitro and in Vivo. J. Med. Chem. 2004, 47, pp. 175-187.

Matrin, M.B., et al. Bisphosphonates Inhibit the Growth of *Trypanosoma brucei, Trypanosoma cruzi, Leishmania donovani, Toxoplasma gondii,* and *Plasmodium falciparum*: A Potential Route to Chemotherapy. J. Med. Chem. 2001, 44, pp. 909-916.

Martin, M.B., et al. Activity of Bisphosphonates against *Trypanosoma brucei* rhodesiense. J. Med. Chem. 2002, 45, pp. 2904-2914.

Sanders, J.M. et al. Pyridinium-1-yl Bisphosphonates are Potent Inhibitors of Farnesyl Diphosphate Synthase and Bone Resorption. J. Med. Chem. 2005, 48, pp. 2957-2963 & S1-S3.

Shamra, N.K. et al. Type II Isopentenyl Diphosphate Isomerase: Probing the Mechanism with Alkyne/Allene Diphosphate Substrate Analogues. Biochemistry 2010, 49, pp. 6228-6233.

Thibodeaux, C.J., Lui, H. Unraveling the Mechanisms of Isoprenoid Biosynthetic Enzymes: Mechanistic Studies of the Early Stage Enzymes. CHIMIA, 2009, 63(6), pp. 334-339.

Van Hoof, S., et al. Synthesis of Analogues of (E)-1-Hydroxy-2-methylbut-2-enyl 4-Diphosphate, an Isoprenoid Precursor and Human [gamma][delta] T Cell Activator. J. Org. Chem. 2008, 73, pp. 1365-1370.

Wang, W., Wang, K., et al. Bioorganometallic mechanism of action, and inhibition, of IspH. PANS, 2010, 107(10), pp. 4522-4527.

International Search Report (Form PCT/ISA/210) for corresponding International Application No. PCT/US2010/0529049.

Written Opinion (Form PCT/ISA/237) for corresponding International Application No. PCT/US2010/0529049.

* cited by examiner

Anionic, Thiol and Neutral Series:

ENZYME INHIBITING COMPOUNDS AND METHODS

RELATED APPLICATIONS

This application is a national stage filing under 35 U.S.C. §371 of PCT/US2010/052049, filed Oct. 8, 2010, which claims priority under 35 U.S.C. §119(e) to U.S. Provisional Patent Application No. 61/249,929, filed Oct. 8, 2009, which applications are incorporated herein by reference in their entirety.

GOVERNMENT SUPPORT

This invention was made with government support under Grant Nos. GM073216, GM65307, and AI074233, awarded by the United States Public Health Service, National Institutes of Health. The United States Government has certain rights in the invention.

BACKGROUND OF THE INVENTION

Enzymes that catalyze the formation of isoprenoids are of interest as drug targets. The Rohmer pathway, also known as the methyl erythritol phosphate or non-mevalonate pathway, is responsible for isoprenoid biosynthesis in most pathogenic bacteria and in malaria parasites, such as *Plasmodium faciparum* (Rohmer et al., *Lipids* 2008, 43(12), 1095; Wiesner and Jomaa, *Current Drug Targets* 2007, 8(1), 3). Enzymes found in the pathway are potentially important as anti-infective drug targets because isoprenoids are essential for survival of these microorganisms and because the non-mevalonate pathway is absent in humans (Williams and McCammon, *Chem. Biol. Drug Des.* 2009, 73(1), 26; de Ruyck and Wouters, *Curr. Protein Pept. Sci.* 2008, 9(2), 117).

The structures and mechanisms of action of six of the eight enzymes present in the pathway are now known. Fosmidomycin, which inhibits the second enzyme in the pathway, has shown promising results for treating malaria (Jomaa et al., *Science* 1999, 285, (5433), 1573; Borrmann et al., *Antimicrobial Agents and Chemotherapy* 2006, 50(8), 2713). An inhibitor of one of the six known enzymes, deoxyxylulose-5-phosphate reductoisomerase, has been used clinically to treat both malaria and *Pseudomonas aeruginosa* infections (Wiesner et al., *Curr. Pharm. Des.* 2008, 14, 855; Cheng et al., *Biochem. Pharmacol.* 1973, 22, 3099).

Less is known, however, about the structures and mechanism of action of the last two enzymes in the pathway: IspG and IspH. IspG is E-4-hydroxy-3-methyl-but-2-enyl diphosphate (HMBPP) synthase, EC 1.17.1.1, also known as GcpE. IspH is E-4-hydroxy-3-methyl-but-2-enyl diphosphate (HMBPP) reductase, EC 1.17.1.2, also known as LytB. The penultimate enzyme is IspG, which catalyzes the $2H^+/2e^-$ reduction of methylerythritol-cyclo-diphosphate (MEcPP, 1) to HMBPP (2), while the terminal enzyme, IspH, catalyzes the $2H^+/2e^-$ reduction of HMBPP (2) to isopentenyl diphosphate (IPP, 3) and dimethylallyl diphosphate (DMAPP, 4) in a ~5:1 ratio.

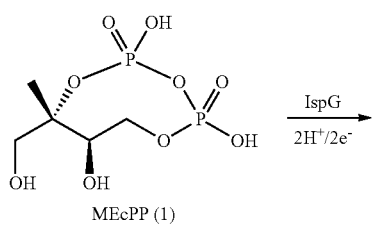

MEcPP (1)

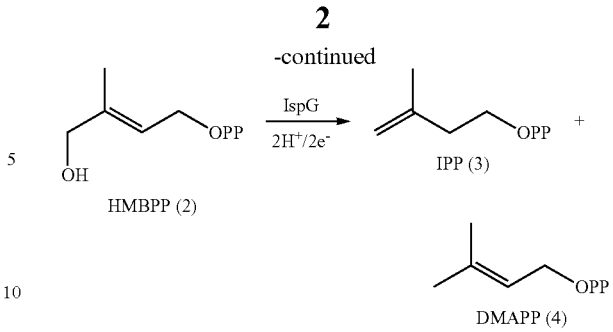

The structure of IspG has not yet been reported, while two structures have been published for IspH, one from *Aquifex aeolicus* (Rekittke et al., *J. Am. Chem. Soc.* 2008, 130, 17206), and the other from *E. coli* (Grawert et al., *Angew. Chem. Int. Ed. Engl.* 2009, 48(31), 5756). According to these reports, both structures contain $Fe_3S_4$ clusters. However, these observations are in contrast to the conclusions drawn from both Mössbauer spectroscopy (Xiao et al., *J. Am. Chem. Soc.* 2009, 131(29), 9931) and EPR spectroscopy (Wolff et al., *FEBS Lett.* 2003, 541(1-3), 115). Both spectroscopic methods lead to the conclusion that $Fe_4S_4$ clusters are responsible for catalysis. The same conclusion was arrived at from the results of microchemical analyses. It therefore seems possible that the $Fe_4S_4$ cluster, while catalytically active, may be relatively labile, as found, for example, in aconitase and in pyruvate-formation lyase activating factor. To date, there has been only one report of an IspH inhibitor (Van Hoof, *J. Org. Chem.* 2008, 73, 1365), which provided an $IC_{50}$ value of ~1-2 mM.

Accordingly, newly identified inhibitors of isoprenoid biosynthesis enzymes are needed to further study the Rohmer pathway. New compounds are also needed to develop effective therapeutic methods, including methods to inhibit the activity of isoprenoid biosynthesis enzymes, and methods for treating diseases such as malaria and other infections, due to increased resistance to currently known antibiotics.

SUMMARY

The invention provides compounds, compositions, and methods for treating bacterial infections or parasitic infections. The parasitic infection can be a protozoan infection, such as malaria. The compounds and compositions can also be used as antibiotics, for example, to kill bacteria or parasites, or to inhibit their growth or proliferation. The invention further provides inhibitors of isoprenoid biosynthesis enzymes, and methods of inhibiting the activity of isoprenoid biosynthesis enzymes. The compounds can be, for example, alkynyl diphosphate inhibitors of the iron-sulfur proteins IspG or IspH (LytB).

Thus, described herein are potent inhibitors of isoprenoid biosynthesis enzymes, such as IspG and IspH. In some embodiments, the inhibitory compounds include complexation moieties that include heteroatoms or pie systems that can complex with an $Fe_4S_4$ cluster of a protein. For example, the inhibitors can contain alkynyl groups that, based on EPR, $^1H$, $^2H$, $^{13}C$ and $^{57}Fe$ electron-nuclear double resonance (ENDOR) spectroscopy and computational docking, form $\pi/\sigma$ "metallacycle" complexes with the $Fe_4S_4$ clusters of IspH. Such clusters have previously been detected by Mössbauer and EPR spectroscopy. This complexation and the resulting inhibition are of broad general interest because it represents the first potent inhibitor of the IspH enzyme, together with a novel inhibition mechanism, involving bioorganometallic complex formation. In one embodiment, the invention provides a $K_i{\sim}200$ nM inhibitor of the isoprenoid biosynthesis enzyme IspH.

Inhibition of the IspH enzyme LytB, ((E)-4-hydroxy-3-methyl-but-2-enyl diphosphate reductase, EC1.17.1.2), has been achieved by more than 35 different compounds described herein. Several active species included alkynyl diphosphate moieties, including one found to have a $K_i$ of approximately 200 nM. The inhibition by the alkynes can involve $\pi/\sigma(\eta^2$-alkynyl) "metallacycle" complex formation with the unique Fe in an $Fe_4S_4$ cluster. Several cationic species were also inhibitors, however their inhibition may be based on interaction with the active site E126. Similar $\pi/\sigma$ complexes may be involved in IspH catalysis. These results, conclusions, and the data supporting provide a conceptually new approach to targeting other $Fe_4S_4$-cluster containing proteins that are of interest as drug targets.

Accordingly, the invention provides compounds of Formula I and methods of using the compounds of Formula I:

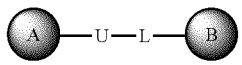

(I)

wherein

A is H; OH; halo; $(C_1\text{-}C_4)$alkyl; $(C_3\text{-}C_8)$cycloalkyl; $CF_3$; $N(R^x)_2$; $(C_1\text{-}C_4)$alkyl substituted by hydroxy, halo, amino, or nitro; 2-oxirane; $-CO_2R^y$; $-CH(CO_2R^y)_2$; $-C(=O)$ $CO_2R^y$; (hydroxylamino)carbonyl; hydroxylamino(sulfonyl); $-S(=NH)_2$-Me; N-carbaldehye-hydroxylamino; aryl, aroyl, heteroaryl, or heterocycle; or A is $-(CH_2)_n-C\equiv C-R^1$ where n is 0-3 and $R^1$ is H, OH, $(C_1\text{-}C_4)$alkyl, $(C_3\text{-}C_8)$ cycloalkyl, $CF_3$, or $N(R^x)_2$;

U is $-C\equiv C-$, $-C\equiv C-C\equiv C-$, or optionally absent if A is $-(CH_2)_n-C\equiv C-R^1$;

L is a direct bond or a divalent radical of the formula $-W-Z-W-$;

wherein each W is independently $-N(R')C(=O)-$, $-C(=O)N(R')-$, $-OC(=O)-$, $-C(=O)O-$, $-O-$, $-S-$, $-S(O)-$, $-S(O)_2-$, $-N(R')-$, $-C(=O)-$, $-(CH_2)_n-$ where n is 1-3, $-(CX^*_2)-$, $-(CH_2)_n-(CX^*_2)-$ where n is 1-3, or a direct bond; and Z is a divalent moiety selected from $(C_1\text{-}C_{12})$alkyl, $(C_2\text{-}C_{12})$alkenyl, $(C_2\text{-}C_{12})$alkynyl, $(C_3\text{-}C_8)$cycloalkyl, $(C_6\text{-}C_{10})$aryl, $-N(R')C(=O)-$, $-C(=O)N(R')-$, $-OC(=O)-$, $-C(=O)O-$, $-N(R')-$, $-C(=O)-$, $-(CX^*_2)-$, $-(CH_2)_n-(CX^*_2)-$ where n is 1-3, $-(OCH_2-CH_2)_n-$ where n is 1 to about 10, $-C(O)NH(CH_2)_n-$ where n is 1 to about 6, $-OP(O)(OH)O-$, $-OP(O)(OH)O(CH_2)_n-$ where n is 1 to about 6, $-OP(O)(OH)OCH_2CH(OH)CH_2-$, $-N^+(Me)_2(CH_2)_n-$ where n is 1 to about 6; or $(C_1\text{-}C_{12})$alkyl, $(C_2\text{-}C_{12})$alkenyl, $(C_2\text{-}C_{12})$alkynyl, or $-(OCH_2-CH_2)_n-$ optionally interrupted between two carbons, or between a carbon and an oxygen, with a $(C_3\text{-}C_8)$cycloalkyl, heteroaryl, heterocycle, or $(C_6\text{-}C_{10})$aryl group, where n is 1 to about 6; or Z is a direct bond;

B is a pyrophosphate group; a phosphonic acid group; a drug moiety; a moiety of Formula I-A; a moiety of Formula I-B; or an independently defined moiety A;

each $R^x$ is independently H, $(C_1\text{-}C_4)$alkyl, $(C_1\text{-}C_4)$alkanoyl, or $-(C_1\text{-}C_4)$alkyl(aryl);

each $R^y$ is independently H, $(C_1\text{-}C_4)$alkyl, or $(C_3\text{-}C_8)$cycloalkyl;

each X* is independently H, OH, $NH_2$, halo, $(C_1\text{-}C_4)$alkyl, or $-(CH_2)_n-CO_2R^y$ wherein n is 0-2; or the two X* groups together are $=C-CO_2R^y$; and each R' is independently H, $(C_1\text{-}C_6)$alkyl, or a nitrogen protecting group;

wherein any alkyl, cycloalkyl, aryl, heteroaryl, or heterocycle is optionally substituted with one or more hydroxy, halo, amino, nitro, trifluoromethyl, trifluoromethoxy, carboxy, carbonyl, thiocarbonyl, $=$N-Me, $(C_1\text{-}C_4)$alkyl, or $(C_1\text{-}C_4)$alkoxy groups, or a combination thereof;

or an anion, cation, salt or solvate thereof.

The group B can be a moiety of Formula I-A:

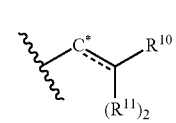

(I-A)

wherein $R^{10}$ is $-CO_2H$ or $P(O)(OH)_2$;

each $R^{11}$ is independently H, OH, $NH_2$, halo, $(C_1\text{-}C_4)$alkyl, $-(CH_2)_n-CO_2R^y$ where n is 0-2, or one $R^{11}$ is absent when the dashed line is a bond; or the two $R^{11}$ groups together are $=C-CO_2R^y$;

the dashed line is an optional bond that forms a double bond to C* when the bond is present; and C* is CH when the dashed line is a bond, and is absent when the dashed line is not present.

The group B can also be a moiety of Formula I-B:

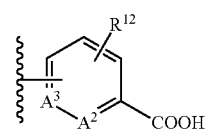

(I-B)

wherein $R^{12}$ is H, OH, halo, or $-(CH_2)_n-CO_2R^y$ where n is 0-2; and $A^2$ and $A^3$ are each independently C, CH, N, $N^+(O^-)$, or $N^+(Me)$.

In various embodiments, the compound of Formula I can be any one of Formulas I-1 to I-22, as illustrated in FIG. 5, where each n is independently 0, 1, 2, 3, 4, or 5. Examples of specific A and B groups are illustrated in FIG. 6.

In some embodiments, the compound of Formula I is a compound of Formula IC:

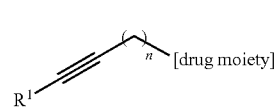

(I-C)

where n is 0 or 1 and the 'drug moiety' is a drug residue that is bonded to the alkyne moiety of the Formula I-C, wherein the drug is selected from selected from alrazagline; selegiline; terbinafine; ethinyl estradiol; norethindrone acetate; desogestrel; levonorgestrel; efavirenz; etonogestrel; norgestimate; or erlotinib. The drug residue is any portion of the drug that is connected to an alkyne that can be the alkyne moiety of Formula I-C. In certain specific embodiments, the compound Formula I is alrazagline; selegiline; terbinafine; ethinyl estradiol; norethindrone acetate; desogestrel; levonorgestrel; efavirenz; etonogestrel; norgestimate; or erlotinib. These drugs are know in the art and are further described in *The Physician's Desk Reference*, 63$^{rd}$ ed. (2009).

In some embodiments, the compound of Formula I is agrocybin, alfaprostol, azafenidin, barban, beraprost, carfimate, cicutoxin, clodinafop-propargyl, danazol, desogestrel, dimethisterone, efavirenz, enanthotoxin, eniluracil, ethchlorvynol, ethinamate, ethinyl estradiol, ethisterone, ethynodiol diacetate, etonogestrel, flumioxazin, gephyrotoxin, gestodene, gestrinone, haloprogin, helenynolic acid, hexapropymate, histrionicotoxin, iloprost, lynestrenol, mepanipyrim, meparfynol, mestranol, methohexital sodium, 2-methyl-3-butyn-2-ol, mifepristone, moxestrol, o-nitrophenylpropiolic acid, norethindrone, norethynodrel, norgestimate, norgestrel, norgestrienone, oxadiargyl, oxenin, oxotremorine, oxybutynin, pargyline, parsalmide, 1-pentol (3-methyl-2-penten-4-yn-1-ol), phthalofyne, pinazepam, prallethrin, propargite, propyzamide, quinestrol, selegiline, tazarotene, terbinafine, thiarubrine A, thiarubrine B, tibolone, tremorine, or xemilofiban. These drugs are know in the art and are further described in *The Merck Index*, 13$^{th}$ Ed. (2001). When one of the aforementioned compounds has a terminal alkyne "H" group, the H can also be replaced by $R^1$, as defined above for Formula I.

Other acetylenic compounds that can be employed in the methods of the invention include cepacin A and/or cepacin B, which can be isolated from the fermentation broth of *Pseudomonas cepacia* SC 11783. Yet other acetylenic compounds include the known enediyne antibiotics.

In some embodiments, the molecular weight of the alkyne or allene compound is less than 500. In other embodiments, the molecular weight is less than 300. In certain embodiments, the molecular weight of the alkyne or allene compound, for example, a compound of a formula described herein (e.g., any one of Formulas I-V and/or their sub-formulas (e.g., those with a letter or number following the Formula Roman numeral)) is about 100 to about 550, about 150 to about 550, about 100 to about 500, about 150 to about 500, about 175 to about 550, about 175 to about 500, about 200 to about 550, about 200 to about 500, about 250 to about 450, about 275 to about 450, about 200 to about 300, about 300 to about 400, about 400 to about 500, about 150 to about 250, about 250 to about 350, about 350 to about 450, or about 450 to about 550.

The invention also provides compounds of Formula II:

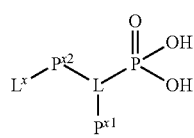
(II)

wherein
 $P^{x1}$ is —P(O)OH$_2$ or absent;
 $P^{x2}$ is a direct bond when $P^1$ is —P(O)OH$_2$ or $P^{x2}$ is —P(O)(OH) when $P^{x1}$ is absent;
 L is O, S, NR$^2$, C(R$^3$)(R$^4$) when $P^{x1}$ is absent; or CH, C—OH, or C-Me when $P^{x1}$ is —P(O)OH$_2$;
 each R$^2$ is independently H or (C$_1$-C$_4$)alkyl;
 each R$^3$ is independently H, halo, or (C$_1$-C$_4$)alkyl;
 each R$^4$ is independently H, halo, or (C$_1$-C$_4$)alkyl; and
 L$^x$ is moiety IIA, IIB, or IIC:

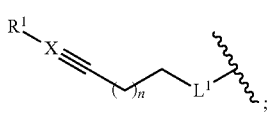
(II-A)

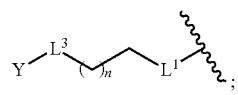
(II-B)

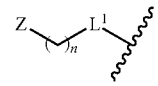
(II-C)

where for moiety II-A:
 R$^1$ is H; CF$_3$; N(R$^x$)$_2$ where R$^x$ is H or (C$_1$-C$_4$)alkyl; (C$_1$-C$_4$)alkyl; or (C$_1$-C$_4$)alkyl substituted by hydroxy, halo, amino, or nitro; or R$^1$ is absent when X is N;
 X is C or N;
 n is 0, 1, or 2;
 L$^1$ is O, S, NR$^2$, or C(R$^3$)(R$^4$);
 each R$^2$ is independently H or (C$_1$-C$_4$)alkyl;
 each R$^3$ is independently H, halo, or (C$_1$-C$_4$)alkyl; and
 each R$^4$ is independently H, halo, or (C$_1$-C$_4$)alkyl;
for moiety II-B:
 Y is 2-oxirane; —OH; —CO$_2$R$^5$ where R$^5$ is H or (C$_1$-C$_4$)alkyl; —N(R$^6$)(R$^7$) where R$^6$ and R$^7$ are each independently H or (C$_1$-C$_4$)alkyl; or aryl or heteroaryl wherein the aryl or heteroaryl is optionally substituted with one or more halo, nitro, amino, trifluoromethyl, trifluoromethoxy, or (C$_1$-C$_4$) alkyl groups, or a combination thereof;
 n is 0, 1, or 2;
 L$^1$ is O, S, NR$^2$, or C(R$^3$)(R$^4$);
 each R$^2$ is independently H or (C$_1$-C$_4$)alkyl;
 each R$^3$ is independently H, halo, or (C$_1$-C$_4$)alkyl;
 each R$^4$ is independently H, halo, or (C$_1$-C$_4$)alkyl; and
 L$^3$ is —(CH$_2$)$_m$—S— where m is 0, 1, 2, or 3; —CR$^8$=CR$^9$— where R$^8$ and R$^9$ are each independently H or Me; or a direct bond; and
for moiety II-C:
 Z is —SH; —N(R$^6$)(R$^7$) where R$^6$ and R$^7$ are each independently H or (C$_1$-C$_4$)alkyl; aryl or heteroaryl wherein the awl or heteroaryl is optionally substituted with one or more halo, nitro, amino, trifluoromethyl, trifluoromethoxy, or (C$_1$-C$_4$)alkyl groups, or a combination thereof; or —C≡C—R$^1$ where R$^1$ is H; CF$_3$; N(R$^x$)$_2$ where R$^x$ is H or (C$_1$-C$_4$)alkyl; (C$_1$-C$_4$)alkyl; or (C$_1$-C$_4$)alkyl substituted by hydroxy, halo, amino, or nitro;
 n is 0, 1, 2, 3, or 4;
 L$^1$ is O, S, NR$^2$, or C(R$^3$)(R$^4$);
 R$^2$ is H or (C$_1$-C$_4$)alkyl;
 R$^3$ is H, halo, or (C$_1$-C$_4$)alkyl; and
 R$^4$ is H, halo, or (C$_1$-C$_4$)alkyl;
or a salt or solvate thereof.

Examples of compounds of Formula II include compounds of Formulas III, IV, and V. Accordingly, the invention also provides compounds Formula III:

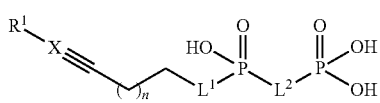
(III)

wherein
 R$^1$ is H; CF$_3$; N(R$^x$)$_2$ where R$^x$ is H, (C$_1$-C$_4$)alkyl; (C$_1$-C$_4$) alkanoyl; or (C$_1$-C$_4$)alkyl substituted by hydroxy, halo, amino, or nitro; or R$^1$ is absent when X is N;
 X is C or N;
 n is 0, 1, or 2;
 L$^1$ is O, S, NR$^2$, or C(R$^3$)(R$^4$);
 L$^2$ is O, S, NR$^2$, or C(R$^3$)(R$^4$);
 each R$^2$ is independently H or (C$_1$-C$_4$)alkyl;
 each R$^3$ is independently H, halo, or (C$_1$-C$_4$)alkyl; and
 each R$^4$ is independently H, halo, or (C$_1$-C$_4$)alkyl;
or a salt or solvate thereof.

In one embodiment, $L^1$ can be O; and $L^2$ is O, $CH_2$ or $CF_2$. In an embodiment, $R^1$ can be H, -Me, or —$CH_2OH$; and $L^2$ is O or $CH_2$. For example, the compound of Formula III can be a compound illustrated in FIG. 1, or an anion, salt or solvate thereof. In other embodiments, $R^1$ can be H, -Me, or —$CH_2OH$; $L^1$ can be O or S; and $L^2$ can be O, $CH_2$ or $CF_2$. For example, the compound of Formula III can be

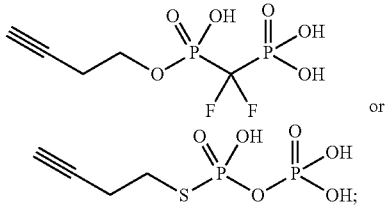

or an anion, salt or solvate thereof.

The invention also provides compounds Formula IV:

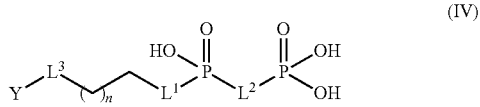

wherein

Y is 2-oxirane; —OH; —$CO_2R^5$ where $R^5$ is H or $(C_1-C_4)$alkyl; —$N(R^6)(R^7)$ where $R^6$ and $R^7$ are each independently H or $(C_1-C_4)$alkyl; or aryl or heteroaryl wherein the aryl or heteroaryl is optionally substituted with one or more halo, nitro, amino, trifluoromethyl, trifluoromethoxy, or $(C_1-C_4)$ alkyl groups, or a combination thereof;

n is 0, 1, or 2;

$L^1$ is O, S, $NR^2$, or $C(R^3)(R^4)$;

$L^2$ is O, S, $NR^2$, or $C(R^3)(R^4)$;

each $R^2$ is independently H or $(C_1-C_4)$alkyl;

each $R^3$ is independently H, halo, or $(C_1-C_4)$alkyl;

each $R^4$ is independently H, halo, or $(C_1-C_4)$alkyl; and $L^3$ is —$(CH_2)_m$—S— where m is 0, 1, 2, or 3; —$CR^8$=$CR^9$— where $R^8$ and $R^9$ are each independently H or Me; or a direct bond; or a cation, anion, salt or solvate thereof.

In one embodiment, Y can be 2-oxirane, —OH, —$CO_2H$, —$CO_2Me$, or —$NMe_2$. In another embodiment, Y can be phenyl, 1-pyridinium, 2-pyridyl, 3-pyridyl, or 4-pyridyl, wherein the phenyl, pyridinium, or pyridyl is optionally substituted by one to five halo groups. For example, the compound of Formula IV can be BPH-293, 1026, 1027, 1029, 1060, 1030, 1032, 1028, 988, 991, 296, 990, 989, 432, or 1031 (see FIGS. 2 and 3), or a cation, anion, salt or solvate thereof.

The invention further provides compounds Formula V:

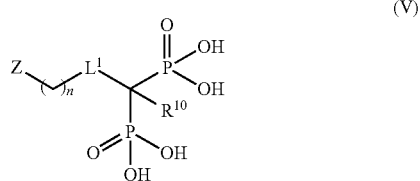

wherein

Z is —SH; —$N(R^6)(R^7)$ where $R^6$ and $R^7$ are each independently H or $(C_1-C_4)$alkyl; awl or heteroaryl wherein the awl or heteroaryl is optionally substituted with one or more halo, nitro, amino, trifluoromethyl, trifluoromethoxy, or $(C_1-C_4)$alkyl groups, or a combination thereof or —C≡C—$R^1$ where $R^1$ is H; $CF_3$; $N(R^x)_2$ where $R^x$ is H or $(C_1-C_4)$alkyl; $(C_1-C_4)$alkyl; or $(C_1-C_4)$alkyl substituted by hydroxy, halo, amino, or nitro;

n is 0, 1, 2, 3, or 4;

$L^1$ is O, S, $NR^2$, $C(R^3)(R^4)$ or —NH—$C(R^3)(R^4)$;

$R^2$ is H or $(C_1-C_4)$alkyl;

$R^3$ is H, halo, or $(C_1-C_4)$alkyl;

$R^4$ is H, halo, or $(C_1-C_4)$alkyl; and $R^{10}$ is H, OH, or Me;

or a salt or solvate thereof.

In one embodiment, $L^1$ can be —$CH_2$— or —NH—. In some embodiments, Z can be —SH, —$NMe_2$, phenyl, 1-pyridinium, 2-pyridyl, 3-pyridyl, or 4-pyridyl, wherein the phenyl, pyridinium, or pyridyl is optionally substituted by one to five halo, methyl, or nitro groups, or a combination thereof. For example, the compound of Formula V can be BPH-2, 21, 9, 200, 290, 299, 297, 650, 639, 272, 993, or 994 (see FIGS. 2 and 3); or a cation, anion, salt or solvate thereof.

In another embodiment, the alkyne or allene compound can be a compound generically described, specifically illustrated, or recited, in U.S. Pat. Nos. 4,588,828 (Bisacchi et al.); 4,654,426 (Bisacchi et al.); or 7,253,192 (Ackermann et al.), as well as U.S. Patent Publication Nos. 2008/0214673 (Glatthar et al.); or 2009/0176781 (Wang et al.); the compounds and preparatory methods of which are incorporated herein by reference.

In one embodiment, a compound as described above can inhibit an isoprenoid biosynthesis enzyme when in contact with the isoprenoid biosynthesis enzyme, for example, in vitro or in vivo. The isoprenoid biosynthesis enzyme can be, for example, E-4-Hydroxy-3-methyl-but-2-enyl diphosphate reductase. The $K_i$ of the compound can be, for example, less than about 30 μM, less than about 20 μM, less than about 10 μM, less than about 5 μM, less than about 2 μM, less than about 1.5 μM, less than about 1 μM, less than about 0.5 μM, less than about 400 nM, less than about 300 nM, or less than about 250 nM.

The invention thus provides methods of inhibiting the activity of an isoprenoid biosynthesis enzyme that has an $Fe_4S_4$ cluster, for example, an $Fe_4S_4$ cluster with one unique Fe—S bond. The methods can include contacting the enzyme with a compound that has an alkyne or an allene moiety, wherein the compound forms a bioorganometallic complex with the unique iron atom of the $Fe_4S_4$ cluster of the isoprenoid biosynthesis enzyme, thereby inhibiting the activity of the enzyme.

The invention also provides methods of treating a bacterial infection or parasitic infection in a mammal, wherein the bacterial infection or parasitic infection is caused by a bacteria or parasite that has of an isoprenoid biosynthesis enzyme that includes an $Fe_4S_4$ cluster, comprising administering to a mammal in need of such treatment an effective amount of a compound described herein, wherein the compound forms a bioorganometallic complex with an iron atom of the $Fe_4S_4$ cluster of the isoprenoid biosynthesis enzyme, thereby inhibiting the activity of the isoprenoid biosynthesis enzyme, thereby treating the bacterial infection or parasitic infection.

The invention further provides methods of killing or inhibiting the growth of a bacteria or a parasite, wherein the bacteria or parasite has of an isoprenoid biosynthesis enzyme that includes an $Fe_4S_4$ cluster. These methods can include contacting the bacteria or parasite with a compound described herein, wherein the compound forms a bioorganometallic complex with an iron atom of the $Fe_4S_4$ cluster of the isoprenoid biosynthesis enzyme, thereby killing or inhibiting the growth of the bacteria or parasite. In these methods, the distance between a π-system of the compound and the unique Fe of the $Fe_4S_4$ cluster in the bioorganometallic complex can be about 4.5 Å or less, 4 Å or less, or about 3.6 Å or less.

The invention therefore provides useful compounds of the formulas described herein, intermediates for the synthesis of such compounds, as well as methods of preparing the compounds, and for preparing compositions of the compounds. In some embodiments, the compounds can be useful as intermediates for the synthesis of other biologically active compounds. The compounds and compositions can also be used to manufacture medicaments useful for the treatment of a disease in a mammal, for example, an infection in a human.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

DETAILED DESCRIPTION

Definitions

Figure 1:
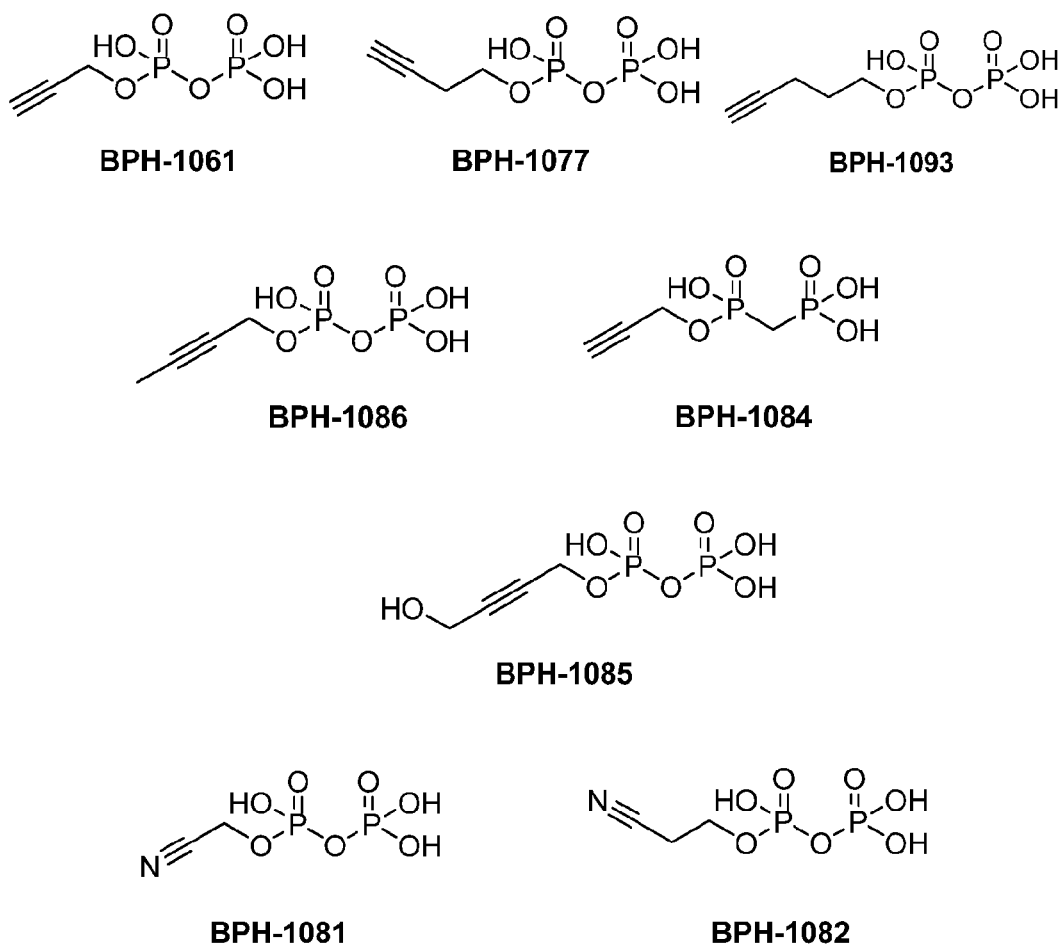
FIG. 1 illustrates several acetylene-containing compounds, according to various embodiments.

As used herein, certain terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", "an example embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect such aspect, feature, structure, moiety, or characteristic in connection with other embodiments, whether or not explicitly described.

The term "and/or" means any one of the items, any combination of the items, or all of the items with which this term is associated.

The singular forms "a," "an," and "the" include plural reference unless the context clearly dictates otherwise. Thus, for example, a reference to "a compound" includes a plurality of such compounds, so that a compound "X" includes a plurality of compounds X. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation. For example, provisos may apply to any of the disclosed categories or embodiments wherein any one or more of the other above disclosed embodiments, species, or elements may be excluded from such categories or embodiments.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment. In addition, unless indicated otherwise herein, a recited range (e.g., weight percents or carbon groups) includes each specific value, integer, decimal, or identity within the range.

The phrase "one or more" is readily understood by one of skill in the art, particularly when read in context of its usage. For example, one or more substituents on a phenyl ring refers to one to five, or one to up to four, for example if the phenyl ring is disubstituted.

The term "contacting" refers to the act of touching, making contact, or of bringing to immediate or close proximity, including at the molecular level, for example, to bring about a chemical reaction or physical change, e.g., in a solution or other reaction mixture, such as in a cellular assay or in the body of a mammal.

An "effective amount" refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art. The term effective amount is intended to include an amount of a compound described herein, or an amount of a combination of compounds described herein, e.g., to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" includes both medical, therapeutic, and/or prophylactic administration, as appropriate. Treating can also include killing or inhibiting the growth of a bacteria or a parasite in a patient that has a bacterial or parasitic infection.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

Specific values listed below for radicals, substituents, and ranges, are for illustration only; they do not exclude other defined values or other values within defined ranges for radicals and substituents. Generic terms include each of their species. For example, the term halo includes and can explicitly be fluoro, chloro, bromo, or iodo.

The term "alkyl" refers to a branched, unbranched, or cyclic hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or optionally substituted, for example, with a substituent described below. The alkyl can also be optionally partially or fully unsaturated. As such, the recitation of an alkyl group can optionally include both alkenyl or alkynyl groups, in certain embodiments. The alkyl can be a monovalent hydrocarbon radical, as described and exemplified above, or it can be a divalent hydrocarbon radical (i.e., an alkylene), depending on the context of its use.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl group can be monovalent or divalent, and can be optionally substituted, for example, by one or more alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 20 carbon atoms, for example, about 6-10 carbon atoms, in the cyclic skeleton. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "aroyl" refers to an aryl-C(=O)— group.

The term "heteroaryl" refers to a monocyclic, bicyclic, or tricyclic ring system containing one, two, or three aromatic rings and containing at least one nitrogen, oxygen or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

Figure 6:
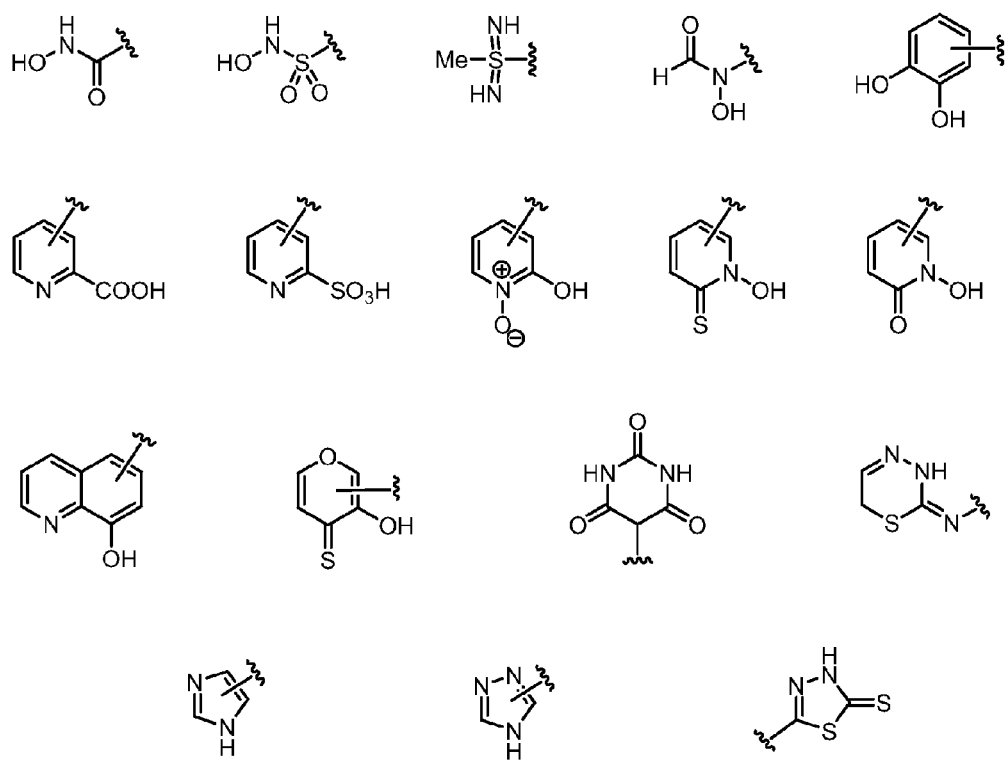
FIG. 6 illustrates several examples of moieties A or B that can be part of Formula I, or a sub-formula thereof, according to various embodiments.

The term "substituted" indicates that one or more (e.g., 1, 2, 3, 4, or 5; in some embodiments 1, 2, or 3; and in other embodiments 1 or 2) hydrogen atoms on the group indicated in the expression using "substituted" is replaced with a "substituent". The substituent can be one of a selection of the indicated group(s), or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl (alkyl)amine, and cyano, as well as the moieties illustrated in FIG. 6. Additionally, suitable substituent groups can be, e.g., —X, —R, —O⁻, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR—S(=O)$_2$O⁻, —S(=O)$_2$OH, —S(=O)$_2$R, —OS(=O)$_2$OR, —S(=O)$_2$NR, —S(=O)R, —OP(=O)O$_2$RR, —P(=O)O$_2$RR—P(=O)(O⁻)$_2$, —P(=O)(OH)$_2$, —C(=O)R, —C(=O)X, —C(S)R, —C(O)OR, —C(O)O⁻, —C(S)OR, —C(O)SR, —C(S)SR, —C(O)NRR, —C(S)NRR, —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group.

The term "solvate" refers to a solid compound that has one or more solvent molecules associated with its solid structure.

Solvates can form when a solid compound is crystallized from a solvent, wherein one or more solvent molecules become an integral part of the solid crystalline matrix. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. A hydrate is a specific type of a solvate. Hydrates can form when a compound is solidified or crystallized in water, wherein one or more water molecules become an integral part of the solid crystalline matrix. The compounds of the formulas described herein can be hydrates.

Isomers

As to any of compound described herein, which contains one or more substituents, it is understood, of course, that such groups do not contain any substitution or substitution patterns that are sterically impractical and/or synthetically non-feasible. The total molecular weight of substituents on a single group will typically be less than about 600, 500, 400, 300, 200, or 100. It will be appreciated that the compounds of the invention can contain asymmetrically substituted carbon atoms, and may be isolated in optically active or racemic forms. It is well known in the art how to prepare optically active forms, such as by resolution of racemic forms or by synthesis from optically active starting materials or by the use of enantioselective catalytic reactions. All chiral, diastereomeric, racemic forms and all geometric isomeric forms of a compound are intended as part of this invention.

One diastereomer may display superior activity compared to another. When required, separation of racemic materials can be achieved by high performance liquid chromatography (HPLC) using a chiral column or by a resolution using a resolving agent such as camphonic chloride, as in Thomas J. Tucker et al., *J. Med. Chem.* 1994, 37, 2437-2444. A chiral compound may also be directly synthesized using a chiral catalyst or a chiral ligand; see, for example, Mark A. Huffman et al., *J. Org. Chem.* 1995, 60, 1590-1594.

Analysis of Enzyme Inhibitors

The nature of the active site Fe/S cluster composition ($Fe_3S_4$ versus $Fe_4S_4$) in IspH enzymes was determined using EPR spectroscopy and activity measurements Inhibitors that target either the active site Fe/S cluster, and/or amino acid residues that are essential for catalysis, were then developed. These inhibitors provide important information for the development of more potent and effective inhibitors.

The Nature of the Fe/S Cluster in IspH: Catalysis and Inhibition Analysis. The X-ray crystallographic structure of IspH (LytB) from *Aquifex aeolicus* has been reported. The enzyme has an open "trefoil"-like structure with an $Fe_3S_4$ cluster at its center. In more recent work, Grävet et al. reported the structure of the *E. coli* IspH, in the presence of diphosphate (PPi). Grävet found that there were large conformational changes in one of the three domains, which formed a "closed structure, with an S(X)N motif (plus one or two His residues) hydrogen bonding to the PPi ligand." As with *A. aeolicus* IspH, there was an $Fe_3S_4$ cluster present. However, these crystallographic results are at odds with previously reported Mössbauer, EPR, microchemical analysis and catalytic activity results, all of which point to an $Fe_4S_4$ cluster as the catalytically active species.

An explanation for this apparent difference is that one Fe may be extended from the cluster during crystallization, but is retained under the rapid-freeze conditions used for EPR and Mössbauer spectroscopy. Lability of Fe in $Fe_4S_4$ clusters has been observed in several other systems including aconitase and pyruvate-formate lyase activators. The presence of a reducing agent (dithionite) can result in re-formation of catalytically active $Fe_4S_4$ clusters.

EPR spectroscopy, combined with catalytic activity determinations, was used to evaluate whether active IspH contains $Fe_4S_4$ clusters. EPR spectra of oxidized [$Fe_3S_4$] clusters have characteristic g~2 spectra characteristic of S=½ spin systems that are found in IspH samples prior to reconstitution (with $Fe^{3+}/S^{2-}$), but represent a small (~10%) spin count. Reduced $Fe_3S_4$ clusters ([$Fe_3S_4$])$^0$) have S=0. To determine to what extent the EPR spectra of IspH could be directly correlated with catalytic activity in samples, the activity *A. aeolicus* IspH that had been reconstituted with varying amounts of $Fe^{3+}/S^{2-}$, or exposed to $O_2$ (to breakdown the Fe/S clusters), was determined. The S=½ ($Fe_4S_4$)$^+$ EPR signal intensity was doubly integrated in reduced samples (i.e., under the conditions used for activity measurements) and their catalytic activity in HMBPP reduction was then determined. There was good correlation between the intensity of the [$Fe_4S_4$]$^+$ S=½ EPR signal and catalytic activity, supporting the results of previous Mössbauer and EPR studies. These results indicated that acetylenes can bind to reduced IspH. To evaluate this, a series of acetylenic compounds were prepared (FIG. 1).

Figure 2:
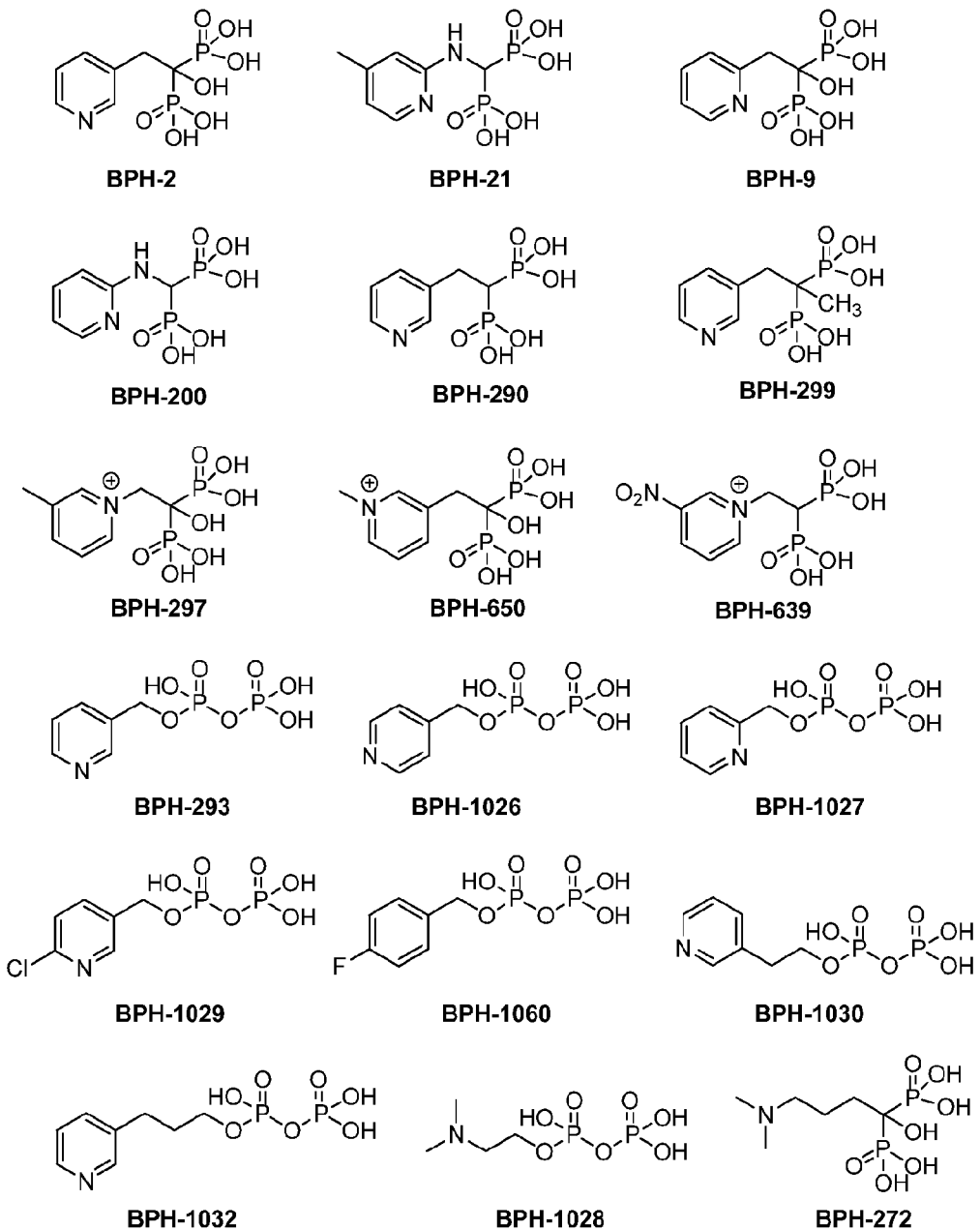
FIG. 2 illustrates several nitrogen-containing compounds, according to various embodiments.

During catalysis by IspH, protons need to be delivered to the active site to protonate the HMBPP 4-OH, as well as protonate to C2 and C4, for IPP and DMAPP formation. It is believed that E126, which is located close to the $Fe_3S_4$ cluster seen in both the open and closed IspH structures, is a likely candidate for an $H^+$ source, and that the essential nature of E126 in catalysis has now been confirmed by site-directed mutagenesis (Grawert et al., *Angew. Chem. Int. Ed. Engl.* 2009, 48(31), 5756). Basic or cationic species may act as IspH inhibitors because they can engage in strong Coulombic or hydrogen bond interactions with E126. Moreover, aromatic residues may also interact with the $Fe_4S_4$ cluster, just as the cyclopentadienide ion does in model $Fe_4S_4$ clusters. Accordingly, a series of aromatic, basic and cationic species were prepared (FIG. 2). These compounds contain anionic backbones to bind to the "PPi" site as observed crystallographically.

Figure 3:
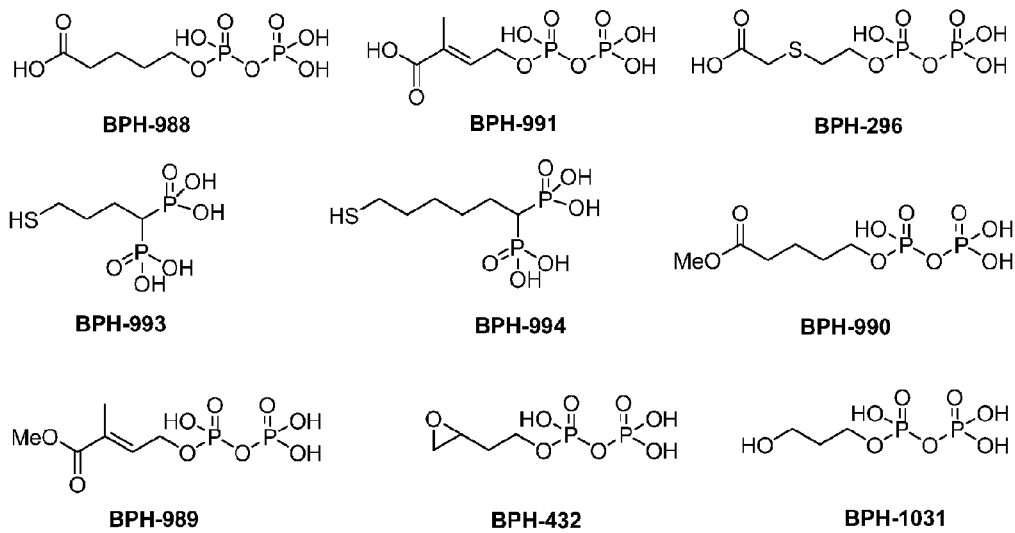
FIG. 3 illustrates several phosphoric acid-containing compounds, according to various embodiments.
Figure 4:
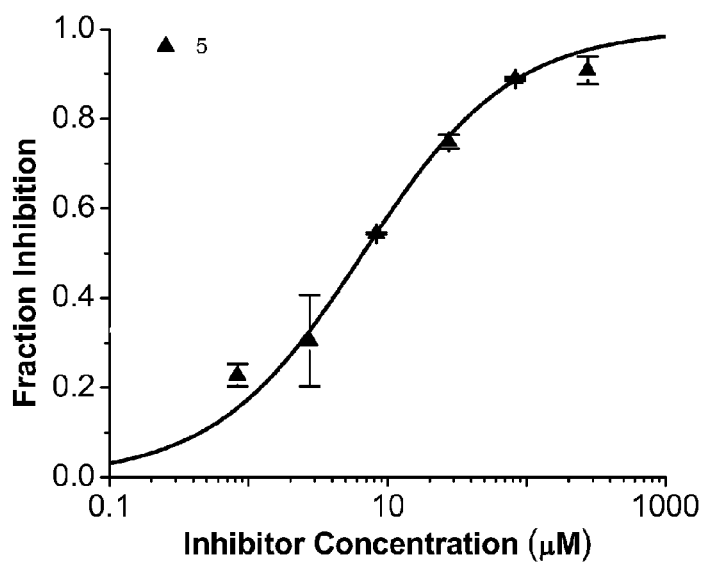
FIG. 4 illustrates the results of IspH inhibition by propargyl diphosphate: $IC_{50}$=6.7 µM; Ki=0.97 µM, carried out according to the procedure described in Example 2.
Figure 5:
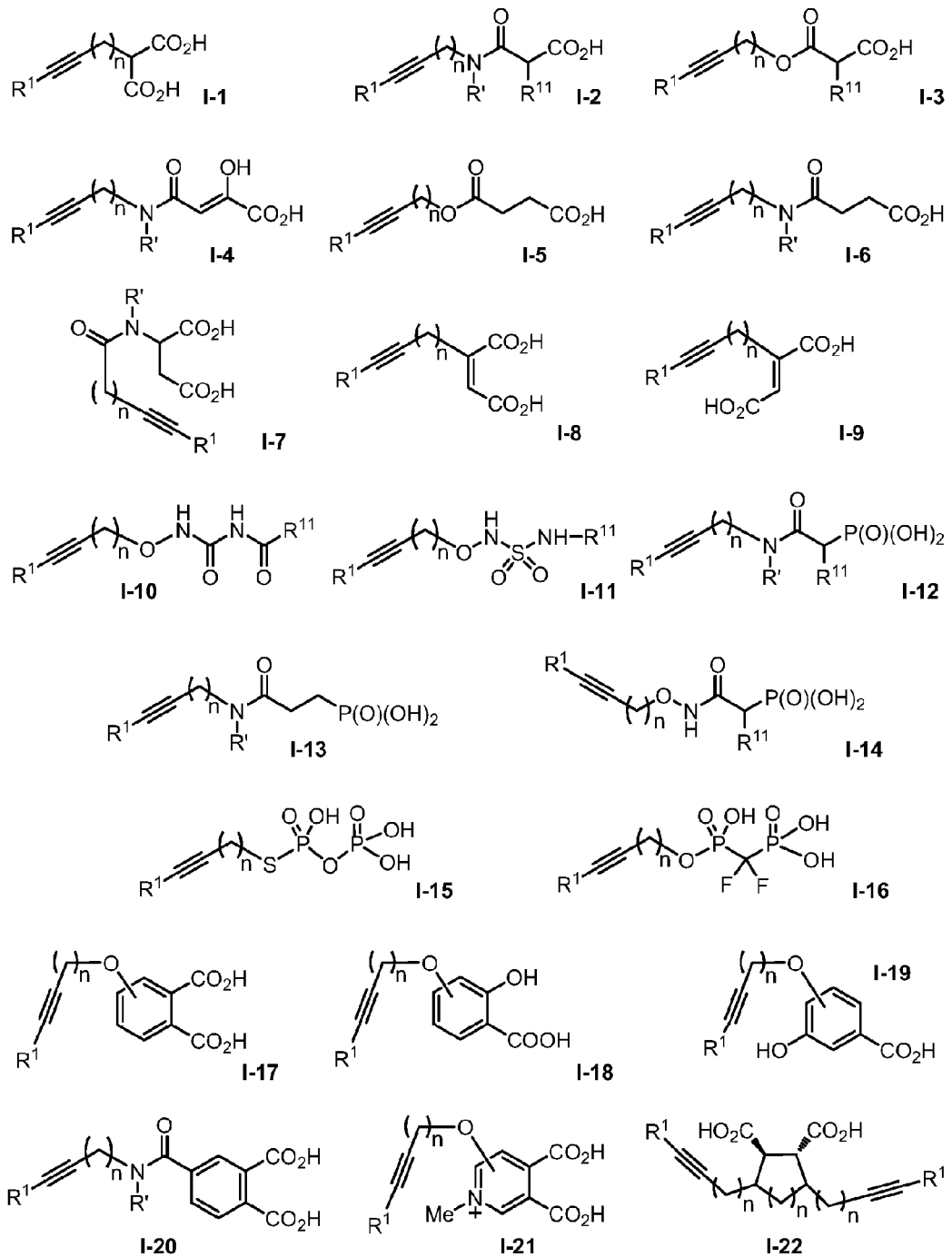
FIG. 5 illustrates Formulas I-1 to I-22, where each n is independently 0, 1, 2, 3, 4, or 5, according to various embodiments.

In addition to E126, the residues H124 and H42 are also essential for catalysis. While the $pK_a$s of these groups in IspH are not known, they may be protonated and/or act as H-bond acceptors. Accordingly, various carboxylic acids, esters, oxiranes, thiols and sulfides containing species were prepared to evaluate their inhibitory activity (FIG. 3).

Acetylenes as IspH Inhibitors. Three acetylenic diphosphates (BPH-1061, BPH-1077, BPH-1093) were prepared and tested for their activity in IspH inhibition. Propargyl alcohol itself had essentially no activity in IspH inhibition ($K_i$>10 mM), however propargyl diphosphate (BPH-1061) showed inhibitory activity, with an $IC_{50}$ of 6.8 µM (corresponding to a $K_i$ of 2.9 µM). Addition of a second $CH_2$ group (BPH-1061) increased activity to a $K_i$=200 nM. The activity decreased with addition of a third methylene group (BPH-1093).

Although crystallographic structures are not currently known for these species, using the Glide docking program, all three compounds are found to bind with their diphosphate groups in the inorganic "PPi" site seen crystallographically, while the alkyne fragments interact with the unique 4$^{th}$ Fe (added computationally), indicating π-complex formation. Similar results were obtained when the diphosphate groups were placed in the "PPi" site manually, followed by the use of molecular mechanics to effect a geometry optimization. Both methods indicate that alkynyl diphosphates can readily fit into the IspH active site, consistent with the inhibition results.

Addition of a terminal methyl group to BPH-1061 (to form BPH-1086) decreased activity, as did conversion of the bridging oxygen to a bridging methylene group (BPH-1084). The latter observation could result because methylene substitution would be expected to change the $pK_a$ values of both phosphate groups and hence, their ability to form H-bonds, as of course does the O→$CH_2$ conversion itself. Similar effects on activity have been observed with HMBPP itself in γδ T cell activation (Amslinger et al., *Immunobiology* 2007, 212, (1), 47-55). The simultaneous presence of both a terminal $CH_2OH$, as well as a terminal $CH_2OPP$ group, reduced activity to approximately the same degree as seen with terminal Me substitution.

The effects of the isoelectronic analogs of the acetylenes (—C≡C—H→—C≡N), cyanides, on IspH inhibition were tested. Alkyl cyanides do react with nitrogenase (Reichenberg et al., *Bioorg. Med. Chem. Lett.* 2003, 13, (7), 1257-60), however there was essentially no inhibition of IspH. Accordingly, acetylenic diphosphates are potent IspH inhibitors. One current lead compound has a $K_i$~200 nM, considerably more potent than any previously reported IspH inhibitor.

Basic IspH Inhibitors. Many anti-infective drugs bind to and can inhibit Fe-containing proteins. For example, antifungals such as miconazole, clotrimazole, ketoconazole, itraconazole and posaconazole all bind to Fe in the P450-dependent lanosterol 14α-demethylase. These compounds are all azoles or imidazoles and bind to form Fe(heme)-N(drug) bonds. The applicants have now found that some IspH inhibitors that contain pyridine side-chains likewise bind to Fe, but in IspH they bind to the unique Fe in the 4Fe-4S cluster. Thus, the compounds described herein can be azole or imidazole-based anti-bacterials analogous to the azole and imidazole anti-fungals. Likewise, forming organometallic complexes between the 4Fe-4S cluster and the inhibitors described herein is a new concept in iron-sulfur protein inhibitor design. This concept can also be applicable to other 4Fe-4S proteins that have a unique 4th iron not liganded to a cysteine residue, such as GcpE (IspG).

In recent work applicants found that pyridine diphosphates were quite promising competitive inhibitors of LytB (and GcpE) with Ki values as low as 9 uM. Using computational docking, it was found that the pyridine bound adjacent the unique 4th Fe.

To investigate this side-chain binding in more detail, the binding of compound BPH-293 to LytB was studied using HYSCORE spectroscopy. The results were quite interesting in that evidence for a large hyperfine interaction with the pyridine 14N was found. 14N signals from the pyridine nitrogen are seen in the (+,−) quadrant with 14N single quantum and double quantum correlation peaks being well resolved. Signals in this quadrant have larger hyperfine couplings (A) than the nuclear Zeeman energies (vL) (A/2>vL to a first order of approximation), and the center of the single quantum correlation peaks is at one half the hyperfine coupling. Therefore, the hyperfine coupling of the pyridine nitrogen is estimated to be ~8-9 MHz. This is quite large, strongly indicating the pyridine nitrogen in BPH-293 is directly bonded to the iron-sulfur cluster of LytB, with the large 14N nitrogen hyperfine coupling being similar to that for directly bonded porphyrin nitrogens in some heme proteins.

A series of cationic and/or basic diphosphates and bisphosphonates, isosteres of the diphosphate group, were then investigated. Several possible leads having activity were identified. These compounds were all 1,1-bisphosphonates with 1-H, 1-Me or 1-OH backbone groups, and pyridine, pyridinium or amino-pyridine side chains (see for example, select compounds in FIGS. 2 and 3). The most active of these compounds was an amino-pyridine, BPH-21 ($K_i$=14 μM), which may include an amidinium-like (protonated) side chain in an actual sample mixture. The modest activity of these bisphosphonates may be due to the "branched" nature of the side chain substitution. That is, in contrast to the results obtained with the alkynyl diphosphates, in which the PPi-side chain can adopt a bent-back or hairpin-like structure, this is not possible for the 1-substituted bisphosphonates, and their cationic groups cannot readily form electrostatic interactions with E126.

A series of pyridinium diphosphates (and one phenyl diphosphate) was then prepared: BPH-293, 1026, 1027, 1029, 1030, and 1060. Based on computational docking results, these compounds fit the IspH active site. The most active compound in the series was BPH-293, a meta-pyridinium diphosphate species having a $K_i$=3.2 μM (better than the best bisphosphonate (BPH-21, $K_i$=14 μM)).

Anionic, Thiols and Other Neutrals as Potential IspH Inhibitors. A third set of compounds was investigated. The compounds synthesized, including two ester controls, are shown in FIG. 3. The most active compound was the carboxylic acid diphosphate BPH-988 (Ki=51 μM). The corresponding esters were less active. Oxirane BPH-432 had similar activity ($K_i$=66 μM) to the pentane thiol BPH-994 ($K_i$=89 μM), while all other compounds had $K_i$>100 μM.

A linear relationship was found between catalytic activity and $[Fe_4S_4]^+$(S=½) EPR signal intensity, which indicates that $Fe_4S_4$ clusters are present in the catalytic mechanism. A series of alkyne diphosphates were prepared and evaluated as potential IspH inhibitors. The most active compound had a $K_i$ value of ~200 nM (BPH-1077), considerably more potent than any previously reported IspH inhibitor. Computational docking revealed that these compounds bind with their disphosphate groups in the "PPi" site seen crystallographically, while their alkyne groups are in close apposition to the $Fe_4S_4$ cluster. The most potent inhibitors have terminal alkyne CH groups, consistent with the observation in low valent ($Fe^I$) complexes that the relative binding energies are PhC≡CH>EtC≡CEt>>PhCH=$CH_2$. This observation indicates that alkynes are useful inhibitors of IspH, displacing HMBPP.

A series of cationic/basic nitrogen-containing bisphosphonates and diphosphates was also investigated. The bisphosphonates had lower activity than the acetylene compounds, presumably due to the orientation of the alkyl substituent at C-1. Bisphosphonates are potent inhibitors of many other prenyl synthases where they bind, typically, to three $Mg^{2+}$ (as do the prenyl diphosphates, during catalysis). However, it is apparent that this binding mode is not found in IspH, where no $Mg^{2+}$ is involved. IspH inhibition by a set of other compounds was also investigated, including acids (to bind to His), thiols, and an oxirane (to bind to the $Fe_4S_4$ cluster, however activities were lower than those of several compounds described above.

These results are of interest because they represent the first potent inhibitors of IspH with $K_i$ (or $IC_{50}$) values ~$10^3$ times less than those and for previously reported inhibitors, and because it has been demonstrated that these compounds can bind to reduced $Fe_4S_4$ clusters. The discovery that alkynes are in fact IspH inhibitors strongly supports the idea that the catalytically active IspH contains active-site $Fe_4S_4$ and not $Fe_3S_4$ clusters, because there is no obvious way in which the alkyne group would bind to the three exposed $S^{2-}$ atoms in such clusters. Formation of π (or π/σ) complexes may be applicable to other $Fe_4S_4^-$ containing proteins such as IspG, the HMBPP synthase, which is also believed to contain a catalytically active $Fe_4S_4$-cluster. Moreover, because π (or π/σ, "metallacycle") complexes are found with the allyl alcohol (the parent alcohol of HMBPP) bound to an Fe/S cluster in the nitrogenase FeMo protein cofactor (similar metallacycle complexes), they may be reactive intermediates or transition states in IspH (and IspG) catalysis.

The compounds described herein provide new inhibitors of IspH, as well as inhibitors of other $Fe_4S_4$ cluster containing proteins, such as IspG and ThiC, and other enzyme that includes an $Fe_4S_4$ cluster. Accordingly, the compounds can be used to treat infections caused by microbes or parasites of a variety of genera, including *Acinetobacter, Actinobacillus, Anaplasma, Bacillus, Bacteroides, Bifidobacterium, Bordetella, Brucella, Burkholderia, Campylobacter, Chlamydia, Clostridium, Corynebacterium, Ehrlichia, Escherichia, Francisella, Fusobacterium, Haemophilus, Helicobacter, Leptospira, Listeria, Mannheimia, Moraxella, Mycobacterium, Mycoplasma, Neisseria, Neorickettsia, Pasteurella, Porphyromonas, Prevotella, Pseudomonas, Psychrobacter, Salmonella, Serratia, Shewanella, Shigella, Tannerella, Treponema, Tropheryma, Vibrio, Wolbachia, Yersinia, Plasmodium,* and *Toxoplasma,* as well as *Eubacterium, Gardnerella, Klebsiella, Peptostreptococcus, Proteus, Providencia,* and *Cryptosporidium* in various embodiments. Parasites are well known and generally include the parasitic protozoans known to infect humans.

Specific examples of species of such genera include, for example, *Acinetobacter* sp., *Actinobacillus pleuropneumoniae, Actinobacillus actinomycetemcomitans, Anaplasma phagocytophilum, Bacillus anthracis, Bacillus cereus, Bacteroides fragilis, Bacteroides thetaiotaomicron, Bifidobacterium longum, Bordetella bronchiseptica, Bordetella pertussis, Brucella melitensis, Brucella suis, Burkholderia cepacia, Burkholderia mallei, Burkholderia pseudomallei, Campylobacter jejuni, Chlamydia trachomatis, Chlamydophila pneumoniae, Clostridium botulinum, Clostridium perfringens, Clostridium diffcile, Clostridium tetani, Corynebacterium diphtheriae, Ehrlichia chaffeensis, Escherichia coli, Francisella tularensis, Fusobacterium nucleatum, Haemophilus ducreyi, Haemophilus influenzae, Helicobacter pylori, Leptospira interrogans, Listeria monocytogenes, Mannheimia haemolytica, Moraxella catarrhalis, Mycobacterium leprae, Mycobacterium smegmatis, Mycobacterium tuberculosis, Mycoplasma penetrans, Neisseria gonorrhoeae, Neisseria meningitides, Neorickettsia sennetsu, Pasteurella multocida, Porphyromonas gingivalis, Prevotella intermedia, Pseudomonas aeruginosa, Pseudomonas putida, Psychrobacter* sp., *Salmonella enterica, Salmonella enteritidis, Salmonella typhimurium, Serratia marcescens, Shewanella putrefaciens, Shigella flexneri, Shigella dysenteriae, Tannerella forsythensis, Treponema denticola, Treponema pallidum, Tropheryma whipplei, Vibrio cholerae, Vibrio vulnificus, Wolbachia* sp., *Yersinia pestis, Yersinia enterocolitica, Plasmodium falciparum, Plasmodium vivax,* and *Toxoplasma gondii,* as well as in some embodiments, *Eubacterium* sp., *Gardnerella vaginalis, Klebsiella pneumoniae, Peptostreptococcus* sp., *Proteus mirabilis, Providencia stuartii,* and *Cryptosporidium parvum.* Thus the compounds described herein can be used to treat infections caused by any one or more of the above genera or species, or the compounds can be used to kill or inhibit the growth of such bacteria or parasite, for example, in vivo, or in vitro, such as in a patient, in a solution, or in or on a grown medium.

Pharmaceutical Formulations

The compounds described herein can be used to prepare therapeutic pharmaceutical compositions. The compounds may be added to the compositions in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 2% to about 60% of the weight of a given unit dosage form. The amount of active compound in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

For topical administration, compounds may be applied in pure form, e.g., when they are liquids. However, it will generally be desirable to administer the active agent to the skin as a composition or formulation, for example, in combination with a dermatologically acceptable carrier, which may be a solid or a liquid.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,608,392 (Jacquet et al.), U.S. Pat. No. 4,992,478 (Geria), U.S. Pat. No. 4,559,157 (Smith et al.), and U.S. Pat. No. 4,820,508 (Wortzman). Such dermatological compositions can be used in combinations with the compounds described herein.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds described herein can be effective antibacterial or anti-protozoan agents. Accordingly, the invention provides therapeutic methods for treating infections in a mammal. The methods can include administering to a mammal that has an infection an effective amount of a compound or composition described herein. A mammal includes a primate, human, rodent, canine, feline, bovine, ovine, equine, swine, caprine, bovine and the like. The ability of a compound described herein to treat an infection may be determined by using assays well known to the art. For example, the design of treatment protocols, toxicity evaluation, data analysis, and quantification of cell kill screens are known.

General Synthetic Methods

Preparation of the compounds described herein can be prepared according to the methods in the Examples below, or may be prepared according to known techniques in the art of organic synthesis. Many alkynes, allenes, and linking groups are commercially available, and/or can be prepared as described in the art. Information regarding general synthetic methods that may be used to prepare the compounds described herein, particularly with respect employing linking groups, may be found in Greg T. Hermanson, *Bioconjugate Techniques*, Academic Press, San Diego, Calif. (1996). Additional useful reactions well known to those of skill in the art are referenced in March's *Advanced Organic Chemistry Reactions, Mechanisms, and Structure*, 5$^{th}$ Ed. by Michael B. Smith and Jerry March, John Wiley & Sons, Publishers; and Wuts et al. (1999), *Protective Groups in Organic Synthesis*, 3$^{rd}$ Ed., John Wiley & Sons, Publishers.

The methods of preparing compounds of the invention can produce isomers in certain instances. Although the methods of the invention do not always require separation of these isomers, such separation may be accomplished, if desired, by methods known in the art. For example, preparative high performance liquid chromatography methods may be used for isomer purification, for example, by using a column with a chiral packing.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Preparation of Enzyme Inhibitors

Reagents used were typically purchased from Aldrich (Milwaukee, Wis.). The purities of compounds investigated were confirmed by either combustion analysis (for solid samples) or by $^1$H and $^{31}$P NMR spectroscopy analysis at 400 or 500 MHz on Varian (Palo Alto, Calif.) Unity spectrometers, using quantitative spin coupling with an internal (imidazole) standard. Cellulose TLC plates were visualized by using iodine or a sulfosalicylic acid-ferric chloride stain.

(E)-Methyl 4-bromo-2-methylbut-2-enoate, propargyl methanesulfonate, but-3-ynyl methanesulfonate and 2-(dimethylamine) ethyl-diphosphate (BPH-1028) were synthesized according to the literature (Davisson et al., *Methods Enzymol.* 1984, 110, 130; Wolff et al., *Tetrahedron Lett.* 2002, 43, 2555; Jackson et al., *Aust. J. Chem.* 1988, 41, 1201; Franceschin et al., *Bio. & Med. Chem.* 2007, 15, 1848; Davisson et al., *J. Org. Chem.* 1986, 51, 4768). The syntheses and characterization of BPH-2, 9, 21, 200, 272, 290, 293, 296, 297, 299, 432, 639 and 650 have been described previously by Oldfield and coworkers (Martin et al., *J. Med. Chem.* 2001, 44, 909; Martin et al., *J. Med. Chem.* 2002, 45, 2904; Ghosh et al., *J. Med. Chem.* 2004, 47, 175; Sanders et al., *J. Med. Chem.* 2005, 48, 2957).

General Procedure for Preparation of Diphosphates

Typically, 0.5-1 mmol of halide or mesylate in a minimum amount of $CH_3CN$ (0.4-0.6 mL) was added dropwise to a stirred solution of 2-3 equiv of tris(tetra-n-butylammonium) hydrogen diphosphate in $CH_3CN$ (3-6 mL), then the reaction mixture was allowed to stir for 2-6 hours at room temperature (~23° C.) and solvent was removed under reduced pressure. The residue was dissolved in cation-exchange buffer (49:1 (v/v) 25 mM $NH_4HCO_3$/2-propanol) and slowly passed over 60-100 m-equiv Dowex AG50W-X8 (100-200 mesh, ammonium form) cation-exchanged resin, pre-equilibrated with two column volumes of the same buffer. The product was eluted with two column volumes of the same buffer, flash frozen, then lyophilized. The resulting powder was dissolved in 50 mM $NH_4HCO_3$. 2-Propanol/$CH_3CN$ (1:1 (v/v)) was added, and the mixture vortexed, then centrifuged for 5 min at 2000 rpm. The supernatant was decanted. This procedure was repeated three times, and the supernatants were combined. After removal of the solvent and lyophilization, a white solid was obtained. Flash chromatography was carried out on a cellulose column.

Prop-2-ynyl diphosphate (BPH-1061). Propargyl methanesulfonate (134 mg, 1 mmol) in $CH_3CN$ (0.5 mL) was added dropwise to a stirred solution of 2.70 g (3.0 mmol) tris(tetra-n-butylammonium) hydrogen diphosphate in $CH_3CN$ (5 mL) at −20° C. The reaction mixture was then slowly warmed to room temperature over 2 h and solvent removed under reduced pressure. Flash chromatography on a cellulose column (4:1:2.4 (v/v/v) 2-propanol/$CH_3CN$/50 mM $NH_4HCO_3$) yielded 47 mg (18%) of a white solid. $^1$H NMR (400 MHz, $D_2O$) δ 2.68 (s, 1H), 4.38 (d, $J_{H,P}$=9.2 Hz, 2H); $^{31}$P NMR (162 MHz, $D_2O$) δ −10.10 (d, J=20.7 Hz), −7.67 (d, J=20.7 Hz).

But-3-ynyl diphosphate(BPH-1077). But-3-ynyl methanesulfonate (148 mg, 1 mmol) in $CH_3CN$ (0.5 mL) was added dropwise to a stirred solution of 1.80 g (2.0 mmol) tris(tetra-n-butylammonium) hydrogen diphosphate in $CH_3CN$ (4 mL) at 0° C. The reaction mixture was allowed to warm to room temperature over 6 h and solvent removed under reduced pressure. Flash chromatography on a cellulose column (2:1:1 (v/v/v) 2-propanol/$CH_3CN$/50 mM $NH_4HCO_3$) yielded 28 mg (10%) of a white solid. $^1$H NMR (400 MHz, $D_2O$): δ 2.16-2.17 (m, 1H), 2.35-2.40 (m, 2H), 3.81-3.84 (m, 2H); $^{31}$P NMR (162 MHz, $D_2O$): δ −9.83 (d, J=17.0 Hz), −7.82 (d, J=15.9 Hz).

Pent-4-ynyl diphosphate (BPH-1093). 1-Bromobut-2-yne (133 mg, 1 mmol) was treated with 2.70 g (3 mmol) tris(tetra-n-butylammonium) hydrogen diphosphate in $CH_3CN$ (4 mL). Flash chromatography on a cellulose column (2:1:1 (v/v/v) 2-propanol/$CH_3CN$/50 mM $NH_4HCO_3$) yielded 103 mg (35%) of a white solid. $^1$H NMR (400 MHz, $D_2O$): δ 1.65-1.70 (m, 2H), 2.13-2.17 (m, 3H), 3.83 (q, J=6.8 Hz, 2H). $^{31}$P NMR (162 MHz, $D_2O$): δ −9.64 (d, J=20.9 Hz), −7.76 (d, J=20.7 Hz).

But-2-ynyl diphosphate (BPH-1086). 1-Bromobut-2-yne (133 mg, 1 mmol) was treated with 2.70 g (3 mmol) tris(tetra-n-butylammonium) hydrogen diphosphate in $CH_3CN$ (4 mL). Flash chromatography on a cellulose column (2:1:1 (v/v/v) 2-propanol/$CH_3CN$/50 mM $NH_4HCO_3$) yielded 112 mg (40%) of a white solid. $^1$H NMR (400 MHz, $D_2O$): δ 1.66 (t, J=2.0 Hz, 3H), 4.34 (dd, $J_{H,P}$=6.4 Hz, J=2.0 Hz, 2H); $^{31}$P NMR (162 MHz, $D_2O$): δ −9.97 (d, J=20.7 Hz), −7.59 (d, J=20.7 Hz).

[[(Prop-2-ynyl) phosphinyl]methyl]phosphonic acid (BPH-1084). Following a procedure similar to that described, propargyl methanesulfonate (134 mg, 1 mmol) was treated with 2.70 g (3 mmol) tris(tetra-n-butylammonium) hydrogen methanediphosphonate in $CH_3CN$ (4 mL). Flash chromatography on a cellulose column (2:1:1 (v/v/v) 2-propanol/$CH_3CN$/50 mM $NH_4HCO_3$) yielded 92.8 mg (35%) of a white solid. $^1$H NMR (500 MHz, $D_2O$): δ 2.00 (t, $J_{H,P}$=12.0 Hz, 2H), 2.70 (t, J=2.0 Hz, 1H), 4.37 (dd, $J_{H,P}$=9.2 Hz, J=2.0 Hz, 2H); $^{31}$P NMR (202 MHz, $D_2O$): δ 15.59 (d, J=9.3 Hz), 20.06 (d, J=10.7 Hz).

4-Hydroxybut-2-ynyl diphosphate (BPH-1085). 4-Chlorobut-2-yn-1-ol (104 mg, 1 mmol) was treated with 2.70 g (3 mmol) tris(tetra-n-butylammonium) hydrogen diphosphate in $CH_3CN$ (4 mL). Flash chromatography on a cellulose column (2:1:1 (v/v/v) 2-propanol/$CH_3CN$/50 mM $NH_4HCO_3$) yielded a white solid. $^1$H NMR (400 MHz, $D_2O$): δ 4.07(s, 2H), 4.31(d, $J_{H,P}$=6.8 Hz, 2H); $^{31}$P NMR (162 MHz, $D_2O$): δ −10.11(d, J=20.8 Hz), −8.85 (d, J=20.7 Hz).

Cyanomethyl diphosphate(BPH-1081). 2-Chloroacetonitrile (75.5 mg, 1 mmol) was treated with 2.70 g (3 mmol) tris(tetra-n-butylammonium) hydrogen diphosphate in $CH_3CN$ (4 mL). Flash chromatography on a cellulose column (2:1:1 (v/v/v) 2-propanol/$CH_3CN$/50 mM $NH_4HCO_3$) yielded 45 mg (17%) of a white solid. $^1$H NMR (400 MHz, $D_2O$): δ 4.56 (d, J=10.4 Hz, 2H); $^{31}$P NMR (162 MHz, $D_2O$): δ −10.25 (d, J=22.0 Hz), −7.37 (d, J=20.7 Hz).

2-Cyanoethyl diphosphate(BPH-1082). 3-Bromopropanenitrile (134 mg, 1 mmol) was treated with 1.80 g (2 mmol) tris(tetra-n-butylammonium) hydrogen diphosphate in $CH_3CN$ (4 mL). Flash chromatography on a cellulose column (2:1:1 (v/v/v) 2-propanol/$CH_3CN$/50 mM $NH_4HCO_3$) yielded 31 mg (11%) of a white solid. $^1$H NMR (400 MHz, $D_2O$): δ 2.68 (t, J=6.4 Hz, 2H), 3.96 (q, J=6.4 Hz, 2H). $^{31}$P NMR (162 MHz, $D_2O$): δ −10.24 (d, J=20.7 Hz), −6.21 (d, J=20.7 Hz).

(Pyridin-4-yl)-methyl-diphosphate (BPH-1026). 4-(Bromomethyl)pyridine (86 mg, 0.5 mmol) was treated with 1.35 g (1.5 mmol) tris(tetra-n-butylammonium) hydrogen diphosphate in $CH_3CN$ (4 mL). Flash chromatography on a cellulose column (3:2 (v/v) 2-propanol/50 mM $NH_4HCO_3$) yielded 65 mg (40%) of a white solid. $^1$H NMR (400 MHz, $D_2O$): δ 4.92

(d, $J_{H,P}$=8.0 Hz, 2H), 7.41 (d, J=6.0 Hz, 2H), 8.34 (d, J=5.6 Hz, 2H); $^{31}$P NMR (162 MHz, D$_2$O): δ −9.66 (d, J=20.7 Hz), −6.49 (d, J=20.7 Hz).

(Pyridin-2-yl)-methyl-diphosphate(BPH-1027). Following a procedure similar to that described, 2-(bromomethyl) pyride (86 mg, 0.5 mmol) was treated with 1.35 g (1.5 mmol) tris(tetra-n-butylammonium) hydrogen diphosphate in CH$_3$CN (4 mL). Flash chromatography on a cellulose column (3:2 (v/v) 2-propanol/CH$_3$CN/50 mM NH$_4$HCO$_3$) yielded 56 mg (35%) of a white solid. $^1$H NMR (400 MHz, D$_2$O): δ 4.91 (d, $J_{H,P}$=7.2 Hz, 2H), 7.28 (t, J=4.8 Hz, 1H), 7.49 (d, J=8.0 Hz, 1H), 7.80 (t, J=8.0 Hz, 1H), 8.28 (d, J=4 Hz, 1H); $^{31}$P NMR (162 MHz, D$_2$O): δ −9.55 (d, J=22.0 Hz), −6.02 (d, J=19.4 Hz).

(6-Chloropyridin-3-yl)-methyl-diphosphate (BPH-1029). 5-(Bromomethyl)-2-chloropyridine (103 mg, 0.5 mmol) was treated with 1.35 g (1.5 mmol) tris(tetra-n-butylammonium) hydrogen diphosphate in CH$_3$CN (4 mL). Flash chromatography on a cellulose column (3:2 (v/v) 2-propanol/50 mM NH$_4$HCO$_3$) yielded 70 mg (40%) of a white solid. $^1$H NMR (400 MHz, D$_2$O): δ 4.82 (d, $J_{H,P}$=7.6 Hz, 2H), 7.29 (d, J=8.4 Hz, 1H), 7.74 (dd, J=8.4 Hz, J=2.4 Hz, 1H), 8.20 (d, J=2.4 Hz, 1H). $^{31}$P NMR (162 MHz, D$_2$O): δ −9.73 (d, J=22.0 Hz), −5.81 (d, J=22.0 Hz).

4-Fluorobenzyl-diphosphate (BPH-1060). 1-(Bromomethyl)-4-fluorobenzene (95 mg, 0.5 mmol) in CH$_3$CN (0.5 mL) was added dropwise to a stirred solution of 1.35 g (1.5 mmol) tris(tetra-n-butylammonium) hydrogen diphosphate in CH$_3$CN (3 mL). Flash chromatography on a cellulose column (2:1:1 (v/v/v) 2-propanol/CH$_3$CN/50 mM NH$_4$HCO$_3$) yielded 74 mg (44%) of a white solid. $^1$H NMR (400 MHz, D$_2$O): δ 4.74 (d, $J_{H,P}$=6.8 Hz, 2H), 6.90-6.95 (m, 2H), 7.25-7.29 (m, 2H); $^{31}$P NMR (161 MHz, D$_2$O): δ −9.74 (d, J=22.0 Hz), −6.18 (d, J=21.9 Hz).

Pyridin-3-yl-ethyl-diphosphate(BPH-1030). 3-(2-Bromoethyl)pyridine (93 mg, 0.5 mmol) was treated with 1.35 g (1.5 mmol) tris(tetra-n-butylammonium) hydrogen diphosphate in CH$_3$CN (4 mL). Flash chromatography on a cellulose column (2:1:1 (v/v/v) 2-propanol/CH$_3$CN/50 mM NH$_4$HCO$_3$) yielded 42 mg (25%) of a white solid. $^1$H NMR (400 MHz, D$_2$O): δ 2.87 (t, J=6.4 Hz, 2H), 4.00 (q, J=6.4 Hz, 2H), 7.33 (1H, t, J=6.4 Hz), 7.79 (1H, d, J=8.0 Hz), 8.24 (1H, s), 8.36 (1H, s); $^{31}$P NMR (162 MHz, D$_2$O): δ −9.78 (1 d, J=20.6 Hz), −7.07 (d, J=20.6 Hz).

Pyridin-3-yl-propyl-diphosphate(BPH-1032). 3-(3-Bromopropyl)pyridine (100 mg, 0.5 mmol) was treated with 1.35 g (1.5 mmol) tris(tetra-n-butylammonium) hydrogen diphosphate in CH$_3$CN (4 mL). Flash chromatography on a cellulose column (4.5:2.5:3.0 (v/v/v) 2-propanol/CH$_3$CN/50 mM NH$_4$HCO$_3$) yielded 57 mg (33%) of a white solid. $^1$H NMR (400 MHz, D$_2$O): δ 1.75-1.89 (m, 2H), 2.65-2.73 (m, 2H), 3.84 (t, J=6.0 Hz, 2H), 7.34-7.36 (m, 1H), 7.74 (d, J=8.0 Hz, 1H), 8.26 (s, 1H), 8.35 (s, 1H). $^{31}$P NMR (162 MHz, D$_2$O): δ −9.49 (d, J=20.7 Hz), −6.87 (d, J=21.9 Hz).

5-Pentanoic acid diphosphate (BPH-988):

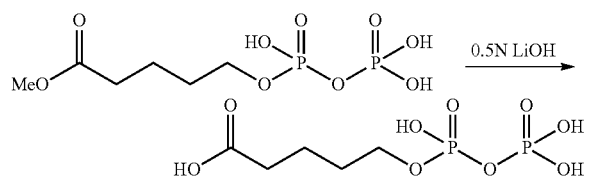

4-(Methoxycarbonyl) butyl diphosphate was dissolved and hydrolyzed in 2 ml 0.5 N LiOH at 4° C. for 20 hours. The solution was neutralized to pH 7.5 with dilute HCl, then lyophilized to yield a white solid (Gil et al., Bio. & Med. Chem. 1999, 7, 901). $^1$H NMR (500 MHz, D$_2$O): δ 1.45-1.47 (4H, m), 2.04-2.08 (t, J=6.5 Hz, 2H), 3.76-3.79 (m, 2H); $^{31}$P NMR (202 MHz, D$_2$O): δ −8.50 (d, J=19.8 Hz), −6.15 (d, J=19.8 Hz).

3-Methyl-but-2-enoic acid diphosphate (BPH-991):

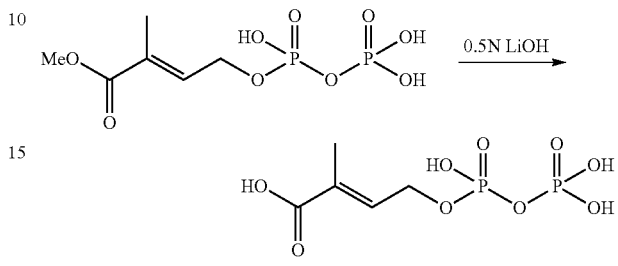

Diphosphate was dissolved and hydrolyzed in 2 ml 0.5 N LiOH at 4° C. for 20 hours. The solution was neutralized to pH 7.5 with dilute HCl, then lyophilized to yield of a white solid (Gil et al., Bio. & Med. Chem. 1999, 7, 901). $^1$H NMR (500 MHz, D$_2$O): δ 1.63 (s, 3H), 4.44 (t, J=6.5 Hz, 2H), 6.19 (t, J=6.0 Hz, 1H);$^{31}$P NMR (202 MHz, D$_2$O): δ −7.71 (d, J=21.2 Hz), −4.02 (d, J=16.8 Hz).

4-(Methoxycarbonyl)butyl diphosphate (BPH-990). Following a procedure similar to that described, methyl 5-bromopentanoate (195 mg, 1 mmol) in CH$_3$CN (0.5 mL) was added dropwise to a stirred solution of 2.70 g (3 mmol) tris(tetra-n-butylammonium) hydrogen diphosphate in CH$_3$CN (4 mL). Flash chromatography on a cellulose column (7:3 (v/v) 2-propanol/50 mM NH$_4$HCO$_3$) yielded 102 mg (30%) of a white solid. $^1$H NMR (500 MHz, D$_2$O): δ 1.43-1.49 (4H, m), 2.25 (2H, t, J=6.0 Hz), 3.49(3H, s), 3.71-3.75 (2H, m); $^{31}$P NMR (202 MHz, D$_2$O): δ −9.36 (d, J=19.8 Hz), −6.66 (d, J=21.2 Hz).

(E)-3-(Methoxycarbonyl)but-2-enyl diphosphate (BPH-989). Following a procedure similar to that described, (E)-methyl 4-bromo-2-methylbut-2-enoate (193 mg, 1 mmol) in CH$_3$CN (0.5 mL) was added dropwise to a stirred solution of 2.70 g (3 mmol) tris(tetra-n-butylammonium) hydrogen diphosphate in CH$_3$CN (4 mL). Flash chromatography on a cellulose column (7:3 (v/v) 2-propanol/50 mM NH$_4$HCO$_3$) yielded 126 mg (37%) of a white solid. $^1$H NMR (500 MHz, D$_2$O): δ 1.67 (s, 3H), 3.59 (s, 3H), 4.51 (t, J=7.0 Hz, 2H), 6.66 (t, J=6.0 Hz, 1H); $^{31}$P NMR (202 MHz, D$_2$O): δ −9.62 (d, J=21.4 Hz), −7.99 (d, J=21.4 Hz).

3-Hydroxypropyl-diphosphate (BPH-1031). 3-Bromopropan-1-ol (139 mg, 1 mmol) was treated with 2.70 g (3 mmol) tris(tetra-n-butylammonium) hydrogen diphosphate in CH$_3$CN (4 mL). Flash chromatography on a cellulose column (3:2(v/v) 2-propanol/50 mM NH$_4$HCO$_3$) yielded 71 mg (24%) of a white solid. $^1$H NMR (400 MHz, D$_2$O): δ 1.67-1.73 (m, 2H), 3.57 (t, J=6.4 Hz, 2H), 3.83-3.89 (m, 2H). $^{31}$P NMR (162 MHz, D$_2$O): δ −9.23 (d, J=21.8 Hz), −6.24 (d, J=20.7 Hz).

Example 2

Enzyme Inhibition Assays

A. aeolicus IspH Protein Purification. BL-21(DE3) cells expressing IspH from A. aeolicus were grown in LB media supplemented with 150 mg/mL ampicillin at 37° C. until the OD600 reached 0.6. Cells were then induced with 200 μg/L anhydrotetracycline and then grown at 20° C. for 15 hours. Cells were harvested by centrifugation (9000 rpm, 8 min, 4° C.) and kept at −80° C. until use. Cell pellets were resuspended and lysed in B-PER (Thermo Scientific, Rockford, Ill.) protein extraction reagent for 1 hour at 4° C. and then centrifuged at 200 000 rpm at 4° C. for 15 minutes. The supernatant was applied to a Ni-NTA column equilibrated with 5 mM imidazole in pH 8.0 buffer containing 50 mM Tris HCl and 150 mM NaCl. After washing with 20 mM imidazole, protein was eluted with 100 mM imidazole. Fractions were collected and dialyzed in pH 8.0 buffer containing 50 mM Tris HCl, 150 mM NaCl, 5% glycerol, and 1 mM DTT, four times. The purified protein was flash-frozen in liquid nitrogen and stored at −80° C. until use.

E. coli IspH Protein Purification. BL21 DE3 (Invitrogen) cells harboring an E. coli IspH construct were grown in LB media at 37° C. until the OD600 reached 0.6. Induction was performed with 200 ng/mL anhydrotetracycline at 20° C. for 15 hours. Cells were harvested by centrifugation at 9000 rpm for 8 min and stored at −80° C. Cell pellets were resuspended and lysed in B-PER protein extraction reagent for about 1 hour at 4° C., and then the lysate was centrifuged at 250 000 rpm for 30 minutes. The supernatant was collected and loaded onto an IBA Strep-tag column equilibrated with buffer W (100 mM Tris.HCl, 150 mM NaCl, pH 8.0). After washing with buffer W, protein was eluted using buffer E (buffer W containing 2.5 mM desthiobiotin). Fractions were collected and dialyzed in pH 8.0 buffer containing 50 mM Tris.HCl, 150 mM NaCl, 5% glycerol, and 1 mM DTT, twice. The purified protein was flashfrozen in liquid nitrogen and stored at −80° C. until use.

Protein Reconstitution. Both A. aeolicus and E. coli IspH proteins as isolated had a very small peak at 410 nm (A280/A410<0.02), so they were reconstituted for further studies. Before reconstitution, protein was transferred into a Coy vinyl anaerobic chamber after being degassed on a Schlenk line. The following steps were performed inside the anaerobic chamber with an oxygen level <2 ppm. In a typical reconstitution experiment, 10 mM DTT and ~0.5 mg of elemental sulfur were added to 3 mL of 0.6 mM protein solution in a pH 8.0 buffer containing 50 mM Tris HCl, 150 mM NaCl, and 5% glycerol. After 1.5 hours under stirring, $FeCl_3$ was slowly added from a 30 mM stock solution to 6 equiv. After 3 hours, an aliquot of the solution was centrifuged and a UV-vis spectrum recorded. If the A410 nm/A280 nm ratio was ≥0.38, the protein was then desalted by passing through a PD10 column. If the ratio was <0.38, more DTT, elemental sulfur, and $FeCl_3$ were added, and the sample was incubated with stirring (for typically ~2 h) until the 410 nm/280 nm absorption ratio was ~0.38. The reconstituted protein was then concentrated by ultrafiltration, and the protein concentration was determined by using a Bio-Rad (Hercules, Calif.) protein assay kit.

IspH inhibition assays. Assays were performed anaerobically at room temperature according to the methods of Altincicek et. al. (FEBS Lett. (2002) 532: 437-440) with the following modifications. To a pH 8.0 buffer solution containing 50 mM Tris HCl, 150 mM NaCl, and 5% glycerol, sodium dithionite was added to 0.4 mM, methyl viologen was added to 2 mM, and IspH was added to 72 nM.

For enzyme assays, various amounts of the test inhibitor (e.g., HMBPP) were added and the reactions were monitored at 732 nm. The initial velocities were fit using the Michaelis-Menten equation using OriginPro 8 (OriginLab Corporation, Northampton, Mass.).

For inhibition assays, various concentrations of inhibitors were added and incubated for 10 minutes prior to addition of 34 µM inhibitor (e.g., HMBPP). Initial velocities at different inhibitor concentrations were then plotted as dose-response curves, and were fitted to the following equation, from which $IC_{50}$ value were determined:

$$y = \frac{1}{1 + \left(\frac{x}{IC_{50}}\right)^{slope}}$$

where y is the fraction inhibition and x is the inhibitor concentration. $K_i$ values were then deduced from the $IC_{50}$ value by using the Cheng-Prusoff equation:

$$K_i = \frac{IC_{50}}{1 + \frac{[S]}{K_M}}$$

where [S] is the inhibitor concentration, and $K_M$ is the Michaelis constant.

EPR Spectroscopy. Samples for EPR spectroscopy were typically 0.3 mM in IspH and were reduced by adding 20 equiv of sodium dithionite followed by incubating for 5 minutes. Glycerol was added to 42.5% (v/v). EPR samples were frozen in liquid nitrogen after reduction. EPR spectra were collected at X-band using a Varian E-122 spectrometer together with an Air Products (Allentown, Pa.) helium cryostat. Data acquisition parameters were typically as follow: field center, 3250 G; field sweep, 800 G; modulation, 100 kHz; modulation amplitude, 5 G; time constant, 32 ms; 60 s/scan; 8 s between scans; and temperature, 15 K. EPR spectral simulations were carried out by using the EasySpin program (Stoll, S.; Schweiger, A.; J. Magn. Reson. 2006, 178, 42).

Docking Calculations. For docking calculations, the IspH target protein (PDB code 3F7T) was prepared using the protein preparation wizard in Maestro 8.0 (Maestro 8.0; Schrodinger, LLC: New York, 2007). Water from the active-site region was removed, as was the diphosphate ligand. The $Fe_3S_4$ cluster was reconstituted computationally to form the $Fe_4S_4$ species as described previously (Rekittke et al., J. Am. Chem. Soc. 2008, 130, 17206), and hydrogen atoms were added to the protein. Hydrogen bonds were optimized to default values, and an energy minimization in MacroModel 9.5 (MacroModel 9.5; Schrodinger, LLC: New York, 2007) was performed only on the protein hydrogens, using default parameters. A receptor grid large enough to encompass all crystallographically observed binding sites was then generated from the prepared target protein. Geometry-optimized ligands were docked using Glide25 extra-precision (XP) mode, and no other constraints were applied. In some instances, we also used the MMFF94 force field (Halgren, T. A.; J. Comput. Chem. 1996, 17, 490) to effect further geometry optimization.

Density Functional Theory Calculations. In order to gain a better understanding of the interaction between the propargyl diphosphate inhibitors and the Fe—S cluster, the published structure of the lowest energy form of allyl alcohol bound to the nitrogenase FeMo cofactor (structure 3 in Pelmenschikov et al., Inorg. Chem. 2008, 47, 6162) was used, converting Mo→Fe, X→S, and allyl→alkynyl as the initial structure. Geometry optimization was performed by using the pure density functional theory (DFT) method with a BPW91 functional, a Wachter's basis (62111111/3311111/3111) for Fe, 6-311G* for all the other heavy atoms, and 6-31G* for the hydrogens, using the Gaussian 09 program (Frisch et al., Gaussian 09, Revision A.01; Gaussian, Inc.: Wallingford Conn., 2009). This method is similar to that used in the calculations of the ligand-bound nitrogenase structures and is the same as that used previously to make accurate predictions of NMR hyperfine shifts and ESR hyperfine couplings, as well as Mossbauer quadrupole splittings and isomer shifts, in various iron-containing proteins and model systems.

Methods of identifying enzyme inhibitors are also described by U.S. Pat. Nos. 7,286,973 (Noel et al.) and 7,534,742 (Eisenreich et al.). Such methods include methods of for screening inhibitors, such as inhibitors of the mevalonate-independent isoprenoid biosynthetic pathway. Other methods of identifying enzyme inhibitors are described by U.S. Pat. No. 7,402,408 (Bacher et al.), which provides, among other information, assays for inhibitors of IspH.

Example 3

Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iii) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (iv) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (v) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

These formulations may be prepared by conventional procedures well known in the pharmaceutical art. It will be appreciated that the above compositions may be varied according to well-known pharmaceutical techniques to accommodate differing amounts of active ingredient 'Compound X'. Aerosol formulation (vi) may be used in conjunction with, for example, a standard metered dose aerosol dispenser. The specific ingredients and proportions are for illustrative purposes. Ingredients may be exchanged for equivalents and proportions may be varied, according to the desired properties of the dosage form of interest.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of Formula III:

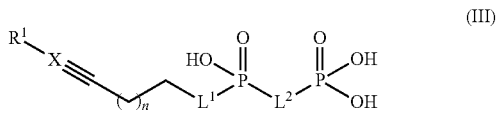

wherein $R^1$ is H; $CF_3$; $N(R^x)_2$ where each $R^x$ is independently H, $(C_1-C_4)$alkyl; $(C_1-C_4)$alkanoyl; or $(C_1-C_4)$alkyl substituted by hydroxy, halo, amino, or nitro; or $R^1$ is absent when X is N;

X is C or N;

n is 0, 1, or 2;

$L^1$ is O, S, $NR^2$, or $C(R^3)(R^4)$;

$L^2$ is O, S, $NR^2$, or $C(R^3)(R^4)$;

each $R^2$ is independently H or $(C_1-C_4)$alkyl;

each $R^3$ is independently H, halo, or $(C_1-C_4)$alkyl; and each $R^4$ is independently H, halo, or $(C_1-C_4)$alkyl;

or a salt or solvate thereof.

2. The compound of claim 1 wherein $L^1$ is O; and $L^2$ is O, $CH_2$ or $CF_2$.

3. The compound of claim 2 wherein $R^1$ is H, -Me, or —$CH_2OH$; and $L^2$ is O or $CH_2$.

4. The compound of claim 3 wherein the compound is:

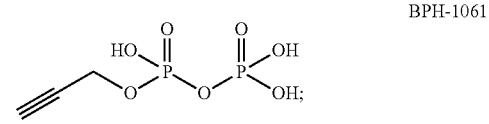

BPH-1061

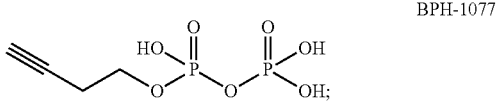

BPH-1077

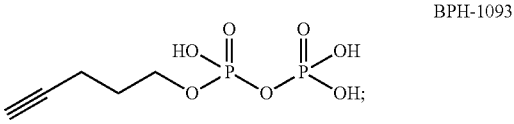

BPH-1093

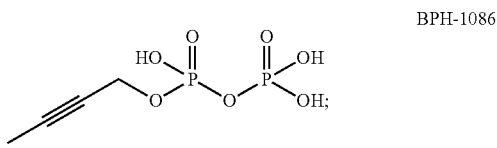

BPH-1086

-continued

BPH-1084
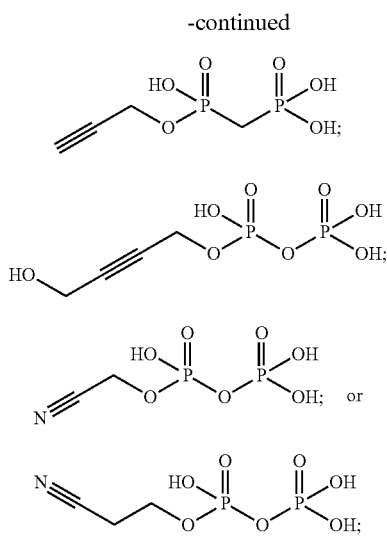

BPH-1085

BPH-1081

BPH-1082 or a salt or solvate thereof.

5. The compound of claim 1 wherein $R^1$ is H, -Me, or —CH$_2$OH; $L^1$ is O or S; and $L^2$ is O, CH$_2$ or CF$_2$.

6. The compound of claim 5 wherein the compound is:

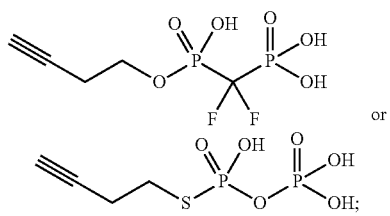

or a salt or solvate thereof.

7. A method of inhibiting the activity of an isoprenoid biosynthesis enzyme that includes an Fe$_4$S$_4$ cluster, comprising contacting the enzyme with a compound of claim 1, wherein the compound forms a bioorganometallic complex with an iron atom of the Fe$_4$S$_4$ cluster of the isoprenoid biosynthesis enzyme, thereby inhibiting the activity of the enzyme.

8. A method of treating a bacterial infection or parasitic infection in a mammal, wherein the bacterial infection or parasitic infection is caused by a bacteria or parasite that has of an isoprenoid biosynthesis enzyme that includes an Fe$_4$S$_4$ cluster, comprising administering to a mammal in need of such treatment an effective amount of a compound of claim 1, wherein the compound forms a bioorganometallic complex with an iron atom of the Fe$_4$S$_4$ cluster of the isoprenoid biosynthesis enzyme of the bacteria or parasite, thereby inhibiting the activity of the isoprenoid biosynthesis enzyme of the bacteria or parasite and treating the bacterial infection or parasitic infection.

9. A pharmaceutical composition comprising a compound of claim 1 and a pharmaceutically acceptable diluent or carrier.

10. The compound of claim 1 wherein $L^2$ is O.
11. The compound of claim 1 wherein $L^2$ is CH$_2$.
12. The compound of claim 1 wherein $L^2$ is CF$_2$.
13. The compound of claim 1 wherein n is 0.
14. The compound of claim 1 wherein n is 1.
15. The compound of claim 1 wherein n is 2.
16. The compound of claim 1 wherein X is C.
17. The compound of claim 1 wherein X is N.
18. The compound of claim 1 wherein $R^1$ is H.
19. The compound of claim 1 wherein $R^1$ is -Me.
20. The compound of claim 1 wherein $R^1$ is —CH$_2$OH.
21. The compound of claim 1 wherein the compound is:

BPH-1061
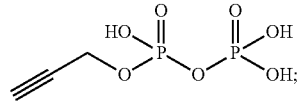

BPH-1077
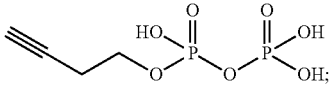

BPH-1093
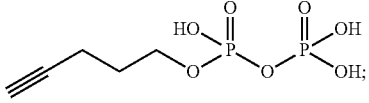

or a salt or solvate thereof.

22. The compound of claim 1 wherein the compound is:

BPH-1086
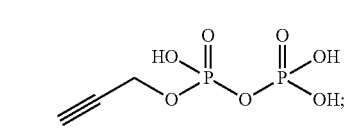

BPH-1085
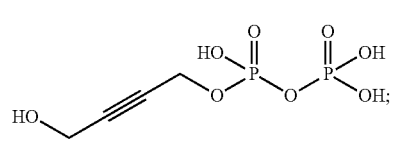

or a salt or solvate thereof.

23. The compound of claim 1 wherein the compound is:

BPH-1084
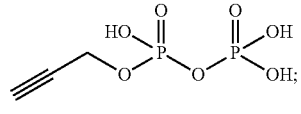

or a salt or solvate thereof.

24. The compound of claim 1 wherein the compound is:

BPH-1081
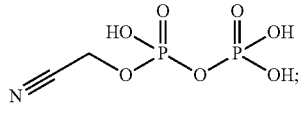

BPH-1082
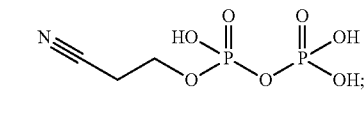

or a salt or solvate thereof.

25. The compound of claim 1 wherein the compound is:
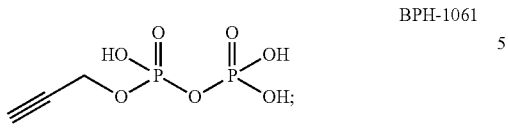
BPH-1061
or a salt or solvate thereof.
26. A pharmaceutical composition comprising a compound of claim 25 and a pharmaceutically acceptable diluent or carrier.
* * * * *